(12) United States Patent
Iwama et al.

(10) Patent No.: US 10,809,178 B2
(45) Date of Patent: Oct. 20, 2020

(54) ANALYSIS DEVICE AND ANALYSIS METHOD

(71) Applicant: JVC KENWOOD CORPORATION, Yokohama-shi, Kanagawa (JP)

(72) Inventors: Shigehiko Iwama, Yokohama (JP); Masahiro Yamamoto, Yokohama (JP); Atsushi Saito, Yokohama (JP)

(73) Assignee: JVC KENWOOD CORPORATION, Yokohama-Shi, Kanagawa (JP)

( * ) Notice: Subject to any disclaimer, the term of this patent is extended or adjusted under 35 U.S.C. 154(b) by 255 days.

(21) Appl. No.: 15/887,387

(22) Filed: Feb. 2, 2018

(65) Prior Publication Data

US 2018/0238790 A1  Aug. 23, 2018

(30) Foreign Application Priority Data

Feb. 22, 2017  (JP) ................................. 2017-030932
Sep. 22, 2017  (JP) ................................. 2017-182037

(51) Int. Cl.
*B01L 3/00*  (2006.01)
*G01N 15/14*  (2006.01)
(Continued)

(52) U.S. Cl.
CPC .......... *G01N 15/1456* (2013.01); *B01L 3/508* (2013.01); *G01N 35/00069* (2013.01);
(Continued)

(58) Field of Classification Search
CPC ........ G01N 15/1456; G01N 35/00069; G01N 33/53; G01N 33/543; G01N 33/567;
(Continued)

(56) References Cited

U.S. PATENT DOCUMENTS 3,736,432 A * 5/1973 Sweet .................... G06M 11/02
                                                377/10
6,327,031 B1 * 12/2001 Gordon ................ G01N 21/253
                                                356/436
(Continued)

FOREIGN PATENT DOCUMENTS

JP          2015-127691 A     7/2015

OTHER PUBLICATIONS

Extended European search report dated Jul. 12, 2018 for corresponding application No. 18157475.7.

*Primary Examiner* — Benjamin R Whatley
*Assistant Examiner* — Curtis A Thompson
(74) *Attorney, Agent, or Firm* — Nath, Goldberg & Meyer; Jerald L. Meyer

(57) ABSTRACT

An analysis device includes a turntable, an optical pickup, and a controller. The turntable holds a disc for specimen analysis having a reaction region on which fine particles binding to substances to be detected are captured per track. The optical pickup emits laser light to the reaction region, receives a reflected light from the reaction region, and generates a reception level signal of the light. The controller sequentially generates a plurality of measurement gate signals per track for counting the number of the fine particles captured on the reaction region, counts the number of the fine particles per measurement gate signal from the reception level signal, compares measurement results obtained in positions having a symmetric relation with each other in the reaction region, and defines a measurement-result-correction target region for correcting the number of the fine particles.

11 Claims, 12 Drawing Sheets

(51) Int. Cl.
*G01N 35/00* (2006.01)
*G01N 33/543* (2006.01)
*G01N 33/567* (2006.01)
*G01N 33/48* (2006.01)
*G01N 33/50* (2006.01)
*G01N 33/53* (2006.01)

(52) U.S. Cl.
CPC ............ *B01L 2200/0647* (2013.01); *B01L 2300/0803* (2013.01); *G01N 33/48* (2013.01); *G01N 33/50* (2013.01); *G01N 33/53* (2013.01); *G01N 33/543* (2013.01); *G01N 33/54366* (2013.01); *G01N 33/567* (2013.01); *G01N 35/00613* (2013.01); *G01N 2015/1486* (2013.01)

(58) Field of Classification Search
CPC .. G01N 33/48; G01N 33/50; G01N 35/00613; G01N 33/54366; G01N 2015/1486; G01N 2015/0277; G01N 2021/936; G01N 2015/1068; G01N 2021/054; G01N 2035/1018; G01N 2291/02433; G01N 2001/2267; G01N 9/28; G01N 2013/0266; G01N 2015/0011; G01N 21/9506; G01N 27/62; G01N 2223/313; B01L 3/508; B01L 2200/0647; B01L 2300/0803

See application file for complete search history.

(56) References Cited

U.S. PATENT DOCUMENTS

| | | | |
|---|---|---|---|
| 6,791,677 B2* | 9/2004 | Kawai | B01L 3/5027 356/73 |
| 2003/0096324 A1* | 5/2003 | Matveev | G01N 15/1475 435/7.21 |
| 2003/0133840 A1* | 7/2003 | Coombs | G01N 15/1475 422/82.05 |

* cited by examiner

ANALYSIS DEVICE AND ANALYSIS METHOD

CROSS REFERENCE TO RELATED APPLICATION

This application is based upon and claims the benefit of priority under 35 U.S.C. § 119 from Japanese Patent Application No. 2017-030932, filed on Feb. 22, 2017, and Japanese Patent Application No. 2017-182037, filed on Sep. 22, 2017, the entire contents of both of which are incorporated herein by reference.

BACKGROUND

The present disclosure relates to an analysis device and an analysis method for analyzing biomaterials such as antigens and antibodies.

Immunoassays are known to quantitatively analyze disease detection and therapeutic effects by detecting particular antigens or antibodies as biomarkers associated with diseases.

Japanese Patent Application Publication No. 2015-127691 (Patent Literature 1) discloses an analysis device in which antibodies that are fixed to a reaction region on a disc for specimen analysis are allowed to bind to antigens in a specimen, and the antigens are labeled by fine particles having antibodies and then are scanned with laser light emitted from an optical pickup so as to detect the fine particles captured on the reaction region. The analysis device disclosed in Patent Literature 1 is an optical disc device utilized for detecting a specimen.

SUMMARY

In the conventional analysis device disclosed in Patent Literature 1, a cartridge is attached to the disc for specimen analysis to form wells. A sample solution and a buffer solution are injected into the wells so that an antigen-antibody reaction is promoted therein to form a reaction region. The wells each function as holders for storing the sample solution and the buffer solution.

When the sample solution and the buffer solution are injected into the wells, bubbles may adhere to the bottom of the wells. If bubbles adhere to the surface of the disc for specimen analysis, which is the bottom of the wells, the antigen-antibody reaction is not promoted in a region to which bubbles adhere (hereinafter, referred to as a bubble region). As a result, it is difficult to accurately measure the fine particles in the reaction region, including the bubble region formed on the disc for specimen analysis.

A first aspect of the embodiments provides an analysis device including: a turntable holding a disc for specimen analysis having a reaction region on which fine particles binding to substances to be detected are captured per track; a turntable drive unit configured to rotate the turntable; a turntable drive circuit configured to control the turntable drive unit; an optical pickup driven in a direction perpendicular to a rotation axis of the turntable, and configured to emit laser light to the reaction region, receive a reflected light from the reaction region, and generate a reception level signal of the light; an optical pickup drive circuit configured to control an operation of the optical pickup; and a controller configured to control the turntable drive circuit and the optical pickup drive circuit, wherein the controller sequentially generates a plurality of measurement gate signals per track for counting a number of the fine particles captured on the reaction region, counts the number of the fine particles per measurement gate signal from the reception level signal, compares measurement results obtained in positions having a symmetric relation with each other in the reaction region, and defines a measurement-result-correction target region for correcting the number of the fine particles.

A second aspect of the embodiments provides an analysis method including: rotating a disc for specimen analysis having a reaction region on which fine particles binding to substances to be detected are captured per track; emitting laser light to the reaction region per track; receiving a reflected light from the reaction region and generating a reception level signal of the light; sequentially generating a plurality of measurement gate signals per track for counting a number of the fine particles captured on the reaction region; counting the number of the fine particles per measurement gate signal from the reception level signal; and comparing measurement results obtained in positions having a symmetric relation with each other in the reaction region, and defining a measurement-result-correction target region for correcting the number of the fine particles.

DETAILED DESCRIPTION

Detection-Target-Substance Capture Unit

Figure 1:
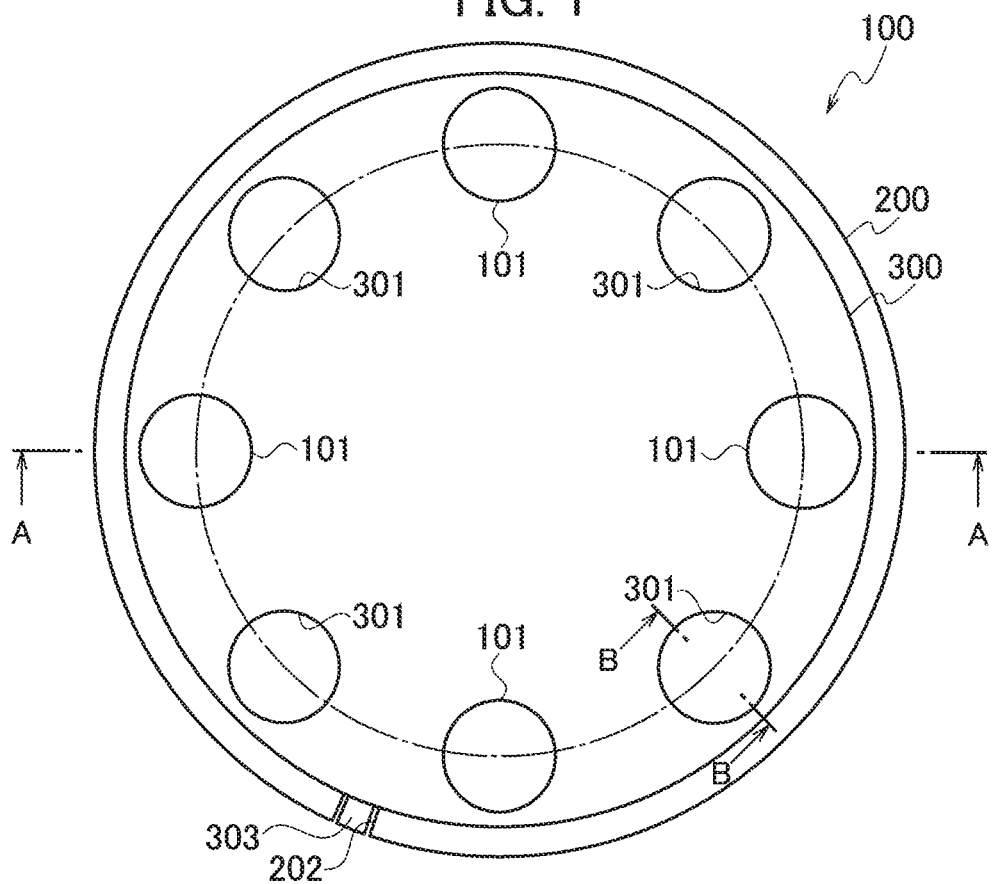
FIG. 1 is a plan view showing a detection-target-substance capture unit.
Figure 2A:
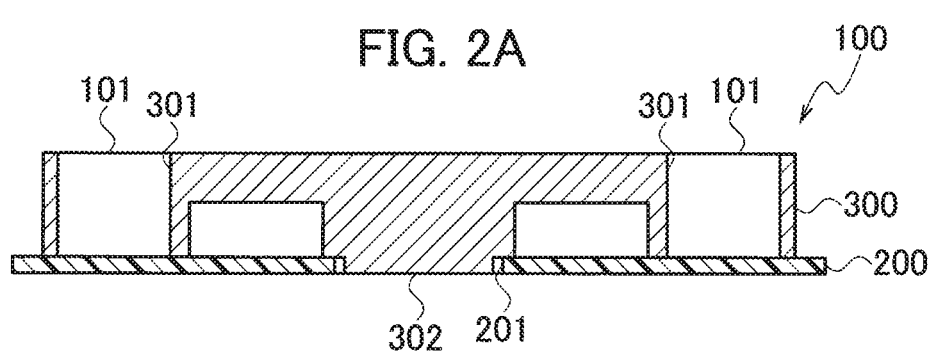
FIG. 2A is a cross-sectional view of the detection-target-substance capture unit taken along line A-A in FIG. 1.
Figure 2B:
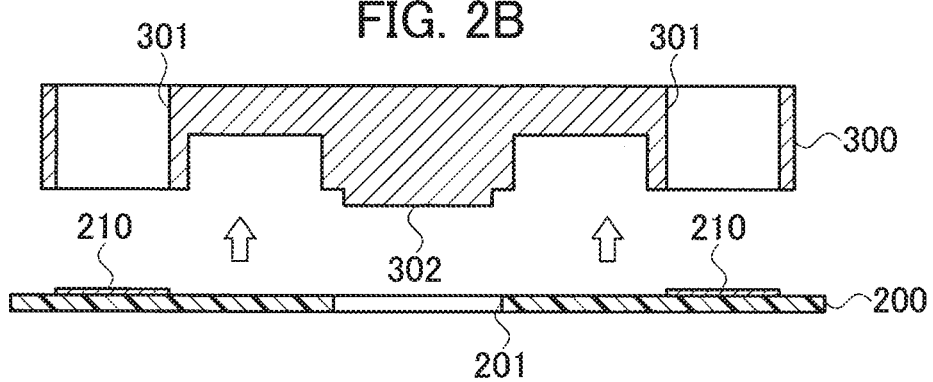
FIG. 2B is a cross-sectional view illustrating a state in which a cartridge is removed from a disc for specimen analysis.
Figure 3:
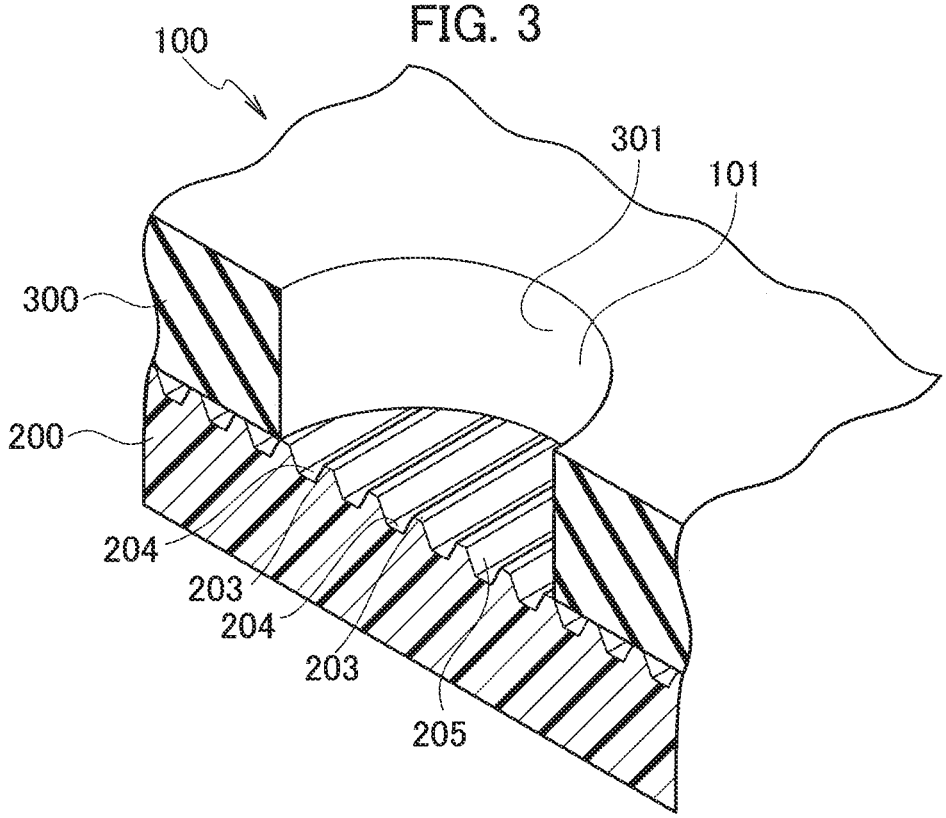
FIG. 3 is an enlarged perspective view showing a well cross-sectioned along line B-B in FIG. 1.

A detection-target-substance capture unit is illustrated below with reference to FIG. 1 to FIG. 3. FIG. 1 is a view showing the detection-target-substance capture unit as viewed from the cartridge side. FIG. 2A is a cross-sectional view of the detection-target-substance capture unit taken along line A-A in FIG. 1. FIG. 2B is a view illustrating a state in which the cartridge is removed from a disc for specimen analysis. FIG. 3 is a partly-enlarged view of a well shown in FIG. 1 taken along line B-B in FIG. 1.

As shown in FIG. 1, the detection-target-substance capture unit 100 includes the disc for specimen analysis 200 (hereinafter, referred to as a "specimen analysis disc 200") and the cartridge 300. The specimen analysis disc 200 is formed into a circular shape having substantially the same dimensions as optical discs such as Blu-ray discs (BDs), digital versatile discs (DVDs), and compact discs (CDs). The specimen analysis disc 200 is formed of resin material such as polycarbonate resin and cycloolefin polymer, commonly used for optical discs. The specimen analysis disc 200 is not limited to the optical discs described above and may be any optical disc according to other embodiments or conforming to prescribed standards.

As shown in FIG. 1, FIG. 2A, and FIG. 2B, the specimen analysis disc 200 has a center hole 201 formed in the middle of the disc, and a slit 202 provided on the circumferential edge of the disc. The slit 202 serves as a reference-position defining portion.

As shown in FIG. 3, the surface of the specimen analysis disc 200 includes a track region 205 provided with projections 203 and recesses 204 alternately arranged in a radial direction. The projections 203 and the recesses 204 are formed in a spiral from the inner side to the outer side of the disc. The projections 203 correspond to lands of an optical disc. The recesses 204 correspond to grooves of an optical disc. The track pitch of the recesses 204 in the radial direction is 320 nm, for example.

As shown in FIG. 1, FIG. 2A, and FIG. 2B, the cartridge 300 is provided with a plurality of cylindrical penetration holes 301 arranged along the circumferential direction. The penetration holes 301 are arranged at regular intervals such that the respective center points are located on the common circle. The cartridge 300 includes a projection 302 in the middle and a projection 303 on the circumferential edge.

When the cartridge 300 is attached to the specimen analysis disc 200, the projection 302 is inserted into the center hole 201 of the specimen analysis disc 200, and the projection 303 is inserted into the slit 202 so that the cartridge 300 and the specimen analysis disc 200 are fitted to each other.

As shown in FIG. 2A and FIG. 3, the detection-target-substance capture unit 100 includes a plurality of wells 101 defined by the insertion holes 301 of the cartridge 300, and the track region 205 of the specimen analysis disc 200. The inner surface of the insertion holes 301 corresponds to the inner surface of the wells 101, and the track region 205 of the specimen analysis disc 200 corresponds to the bottom of the wells 101. The wells 101 each serve as a holder for storing a solution such as a sample solution and a buffer solution. Although FIG. 1 illustrates the detection-target-substance capture unit 100 including eight wells 101, the number of wells 101 is not limited to eight.

As shown in FIG. 2B, the cartridge 300 is detachable from the specimen analysis disc 200. Fine particles for labeling substances to be detected are detected and measured only by use of the specimen analysis disc 200 separated from the cartridge 300.

Formation of Reaction Region

An example of a method of forming reaction regions on the specimen analysis disc 200 of the detection-target-substance capture unit 100 is described below with reference to the flow chart of FIG. 4, FIG. 5A, FIG. 5B, FIG. 5C, FIG. 6, and FIG. 7.

Figure 5A:
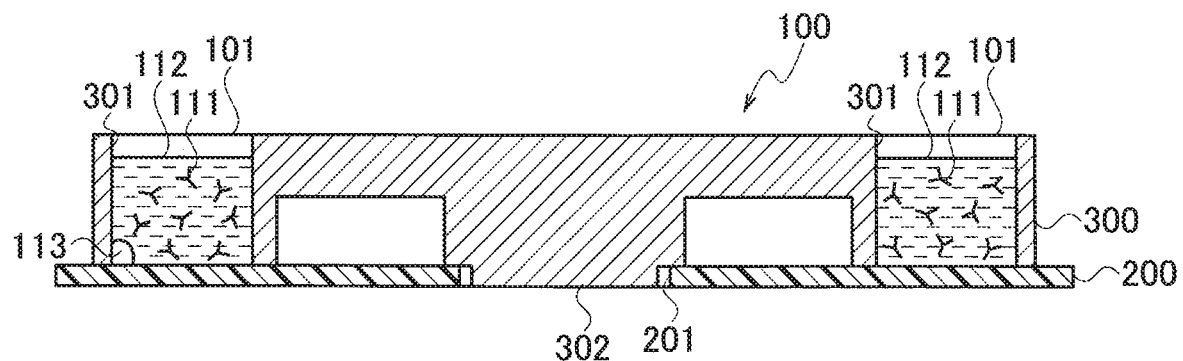
FIG. 5A is a cross-sectional view illustrating a state in which a buffer solution including antibodies is injected into wells in the process of forming the reaction region on the disc for specimen analysis.

In step S101, the operator injects a buffer solution 112 including antibodies 111 into the wells 101 of the detection-target-substance capture unit 100, as shown in FIG. 5A. The operator incubates the solution in the detection-target-substance capture unit 100 for an appropriate time at an appropriate temperature. The antibodies 111 are thus fixed to the track region 205 of the specimen analysis disc 200 which is the bottom of the wells 101.

When the buffer solution 112 is injected, bubbles 113 may adhere onto the track region 205 of the specimen analysis disc 200, which is the bottom of the wells 101. The bubbles 113 tend to adhere to the boundary between the inner surface and the bottom of the wells 101, namely, the boundary between the inner surface of the insertion holes 301 of the cartridge 300 and the track region 205 of the specimen analysis disc 200. When the bubbles 113 adhere to the track region 205, the bubble region prevents the antibodies 111 from being fixed to the track region 205.

The operator drains the buffer solution 112 from the wells 101, and cleans the wells 101 with another buffer solution. The antibodies 111 not fixed to the track region 205 are removed due to the cleaning.

Figure 5B:
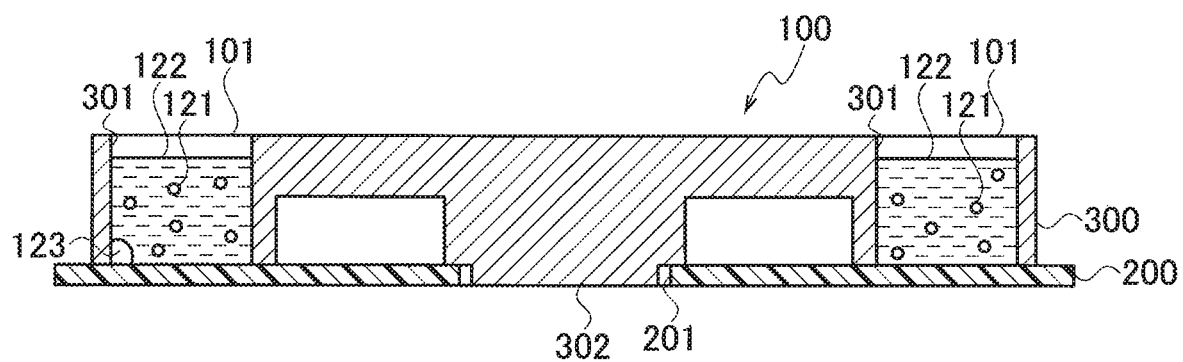
FIG. 5B is a cross-sectional view illustrating a state in which a sample solution including substances to be detected is injected into the wells in the process of forming the reaction region on the disc for specimen analysis.

In step S102, the operator injects a sample solution 122, including substances to be detected 121 (hereinafter, referred to as "detection target substances 121") into the wells 101, as shown in FIG. 5B. The detection target substances 121 are exosomes, for example. The sample solution 122 sometimes does not include the detection target substances 121. The following is the case in which the sample solution 122 includes the detection target substances 121 for illustration purposes.

The operator incubates the solution in the detection-target-substance capture unit 100 for an appropriate time at an appropriate temperature. The detection target substances 121 then specifically bind to the antibodies 111 fixed to the track region 205 by the antigen-antibody reaction. The detection target substances 121 are thus captured on the track region 205.

When the sample solution 122 is injected, bubbles 123 may adhere onto the track region 205 of the specimen analysis disc 200, which is the bottom of the wells 101. The bubbles 123 tend to adhere to the boundary between the inner surface and the bottom of the wells 101, namely, the boundary between the inner surface of the insertion holes 301 of the cartridge 300 and the track region 205 of the specimen analysis disc 200.

When the bubbles 123 adhere to the track region 205, the bubble region prevents the detection target substances 121 from binding to the antibodies 111 fixed to the track region 205. As a result, the detection target substances 121 in the bubble region are not captured on the track region 205.

When the bubble region is formed in the track region 205 in step S101, the antibodies 111, which are to bind to the detection target substances 121, are not fixed to the track region 205 in the bubble region. The detection target substances 121 are thus not captured on the track region 205 in the bubble region formed in step S101, even when the bubbles 123 do not adhere to the track region 205 when the sample solution 122 is injected.

The operator drains the sample solution 122 from the wells 101, and cleans the wells 101 with a buffer solution. The detection target substances 121, not binding to the antibodies 111 and dispersed in the sample solution 122, and the detection target substances 121 adhering to the track region 205 by non-specific binding, which is not the antigen-antibody reaction, are removed due to the cleaning.

Figure 5C:
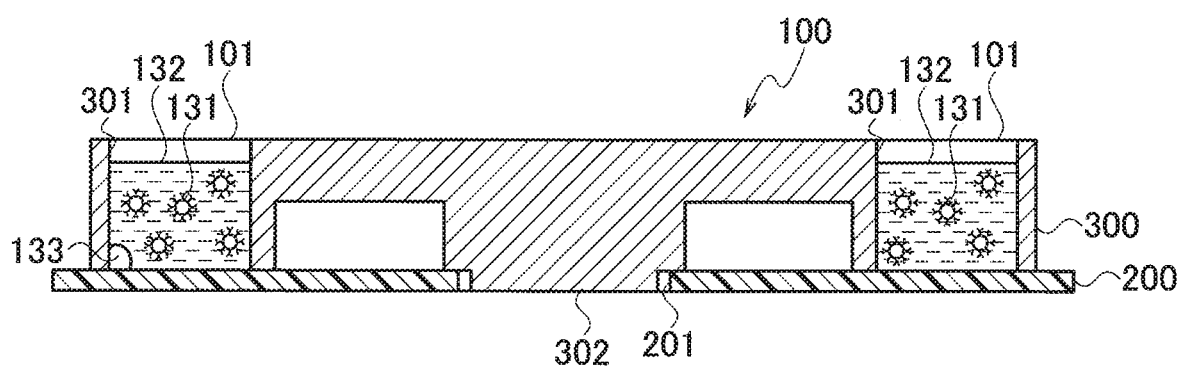
FIG. 5C is a cross-sectional view illustrating a state in which a buffer solution including fine particles is injected into the wells in the process of forming the reaction region on the disc for specimen analysis.

In step S103, the operator injects a buffer solution 132 including fine particles 131 serving as labels into the wells 101, as shown in FIG. 5C. The surfaces of the fine particles 131 are provided with antibodies which specifically bind to the detection target substances 121 by the antigen-antibody reaction.

The operator incubates the solution in the detection-target-substance capture unit 100 for an appropriate time at an appropriate temperature. The fine particles 131 specifically bind to the detection target substances 121 captured on the track region 205 by the antigen-antibody reaction. The fine particles 131 binding to the detection target substances 121 are thus captured on the track region 205, more particularly, on the recesses 204 of the track region 205.

When the buffer solution 132 is injected, bubbles 133 may adhere onto the track region 205 of the specimen analysis disc 200, which is the bottom of the wells 101. The bubbles 133 tend to adhere to the boundary between the inner surface and the bottom of the wells 101, namely, the boundary between the inner surface of the insertion holes 301 of the cartridge 300 and the track region 205 of the specimen analysis disc 200. When the bubbles 133 adhere to the track region 205, the bubble region prevents the fine particles 131 from binding to the detection target substances 121 captured on the track region 205. As a result, the fine particles 131 in the bubble region are not captured on the track region 205.

When the bubble region is formed in the track region 205 in step S101 or step S102, the detection target substances 121, which are to bind to the fine particles 131, are not fixed to the track region 205 in the bubble region. The fine particles 131 are thus not captured on the track region 205 in the bubble region formed in step S101 or step S102, even when the bubbles 133 do not adhere to the track region 205 when the buffer solution 132 is injected.

The operator drains the buffer solution 132 from the wells 101, cleans the wells 101 with another buffer solution, and dries the wells 101. The fine particles 131 not binding to the detection target substances 121 and dispersed in the buffer solution 132 are removed due to the cleaning.

In step S104, the operator separates the cartridge 300 and the specimen analysis disc 200 of the detection-target-substance capture unit 100, as shown in FIG. 2B. The specimen analysis disc 200 is provided with a plurality of circular reaction regions 210 corresponding to the respective wells 101.

Figure 6:
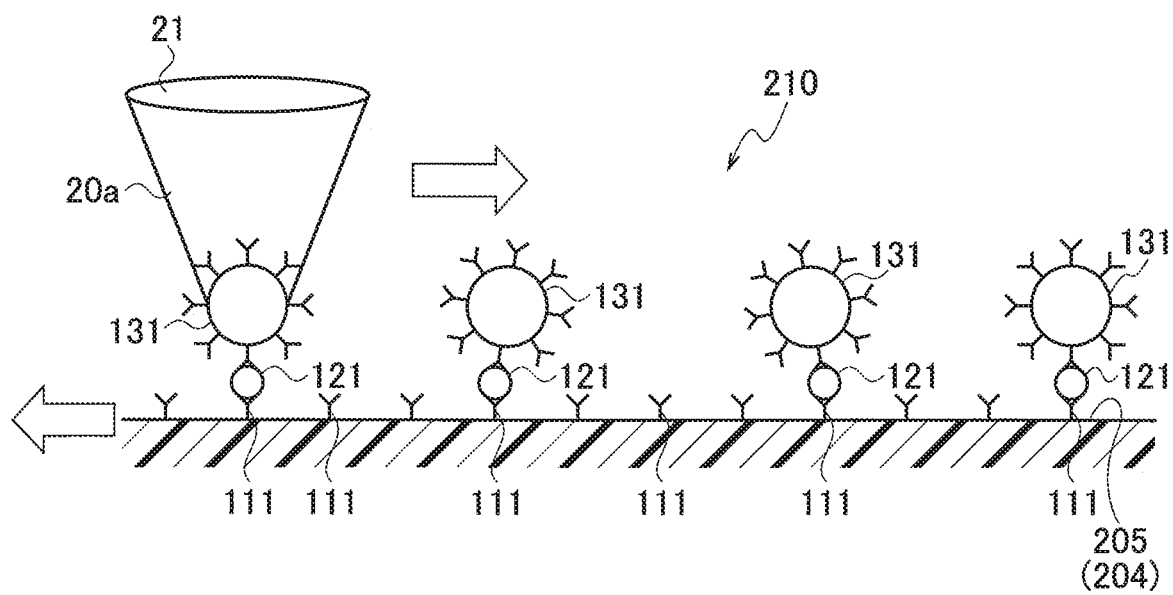
FIG. 6 is a schematic cross-sectional view illustrating a state in which the substances to be detected are captured and sandwiched between the antibodies and the fine particles in a recess of a track region.
Figure 7:
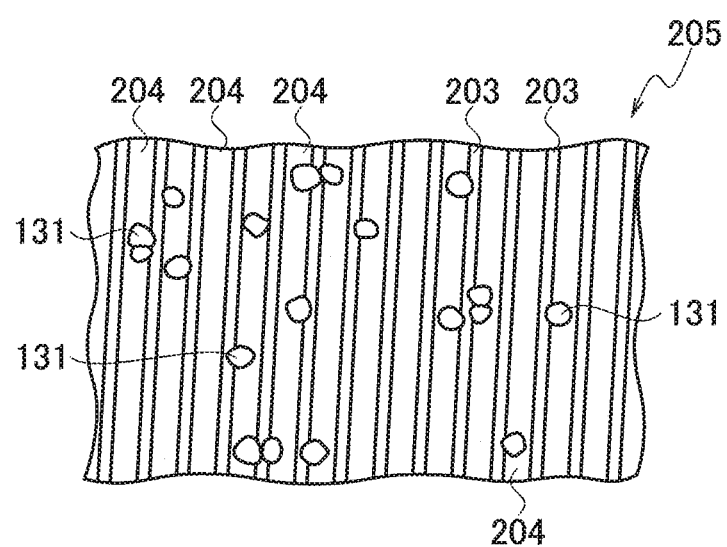
FIG. 7 is a schematic plan view illustrating a state in which the fine particles and the substances to be detected coupled together are captured in recesses of the track region.

As shown in FIG. 6, the fine particles 131 binding to the detection target substances 121 are captured on the recesses 204 of the track region 205 in the reaction region 210. The detection target substances 121 are captured and sandwiched between the antibodies 111 and the fine particles 131 on the recesses 204 of the track region 205. FIG. 7 illustrates a state in which the fine particles 131 binding to the detection target substances 121 are captured on the recesses 204 of the track region 205.

First Embodiment

An analysis device and an analysis method according to a first embodiment are described below with reference to FIG. 8 to FIG. 13. First, the analysis device according to the first embodiment is described with reference to FIG. 8. When the detection target substances 121 are exosomes having a size as small as 100 nm, it is difficult to optically detect the detection target substance 121 directly. The analysis device 1 according to the first embodiment detects and measures the fine particles 131 captured on the reaction regions 210, so as to indirectly detect and measure the detection target substances 121 specifically binding to the fine particles 131.

The analysis device 1 includes a turntable 2, a clamper 3, a turntable drive unit 4, a turntable drive circuit 5, and a reference-position detection sensor 6. The analysis device 1 further includes a guide shaft 7, an optical pickup 20, an optical pickup drive circuit 8, a controller 9, a storage unit 10, and a display unit 11. The analysis device 1 does not necessarily include the display unit 11, and an external display unit may be used instead.

The specimen analysis disc 200 is placed on the turntable 2 with the reaction regions 210 facing down. The clamper 3 is driven in directions separating from and approaching the turntable 1, namely, in the upper and lower directions in FIG. 8. The specimen analysis disc 200 is held by the clamper 3 and the turntable 2 when the clamper 3 is driven in the lower direction.

The turntable drive unit 4 drives the turntable 2 to rotate on the rotation axis C2 together with the specimen analysis disc 200 and the clamper 3. A spindle motor may be used as the turntable drive unit 4. The turntable drive circuit 5 controls the turntable drive unit 4. For example, the turntable drive circuit 5 controls the turntable drive unit 4 such that the turntable 2 rotates at a constant linear velocity together with the specimen analysis disc 200 and the clamper 3.

The reference-position detection sensor 6 is placed adjacent to the circumferential edge of the specimen analysis disc 200. The reference-position detection sensor 6 is an optical sensor such as a photoreflector, for example. The reference-position detection sensor 6 emits detection light 6a toward the circumferential edge of the rotating specimen analysis disc 200, and receives the reflected light from the specimen analysis disc 200.

The reference-position detection sensor 6 detects the slit 202 of the specimen analysis disc 200, generates a reference-position detection signal KS, and outputs the signal to the controller 9. The reference-position detection signal KS is a pulse signal which rises to be on when the slit 202 reaches the detection position of the reference-position detection sensor 6, namely, the position to which the detection light 6a is radiated, and falls to be off when the slit 202 passes through the detection position.

The reference-position detection sensor 6 detects the reference position per rotation period and per track of the specimen analysis disc 200. A transmission-type optical sensor may be used as the reference-position detection sensor 6. The reference-position detection sensor 6 of this type emits the detection light 6a to the specimen analysis disc 200 and receives the detection light 6a passing through the slit 202, so as to detect the reference position per rotation period and per track of the specimen analysis disc 200.

The guide shaft 7 is placed in parallel with the specimen analysis disc 200 in the radial direction of the specimen analysis disc 200. The optical pickup 20 is supported by the guide shaft 7. The optical pickup 20 is driven along the guide shaft 7 in the direction perpendicular to the rotation axis C2 of the turntable 2, in the radial direction of the specimen analysis disc 200, and in parallel with the specimen analysis disc 200.

The optical pickup 20 includes an objective lens 21. The optical pickup 20 emits laser light 20a to the specimen analysis disc 200. The laser light 20a is condensed by the objective lens 21 on the track region 205 provided with the reaction regions 210 on the specimen analysis disc 200.

The optical pickup 20 is driven in the radial direction of the rotating specimen analysis disc 200. The laser light 20a thus scans the recesses 204 corresponding to tracks, as shown in FIG. 6. The optical pickup 20 receives the reflected light from the specimen analysis disc 200. The optical pickup 20 detects a reception level of the reflected light, generates a reception level signal JS, and outputs the signal to the controller 9.

The optical pickup drive circuit 8 controls the operation of the optical pickup 20. The optical pickup drive circuit 8 moves the optical pickup 20 along the guide shaft 7 or moves the objective lens 21 of the optical pickup 20 in the vertical direction.

The controller 9 controls the turntable drive circuit 5 and the optical pickup drive circuit 8. The controller 9 controls the turntable drive circuit 5 to stop or rotate the turntable 2 at a constant linear velocity, for example. The controller 9 controls the optical pickup drive circuit 8 to move the optical pickup 20 to a target position in the radial direction of the specimen analysis disc 200 or adjust the position of the objective lens 21 in the vertical direction so as to condense the laser light 20a on the track region 205. A central processing unit (CPU) may be used as the controller 9, for example.

The controller 9 detects the reference position per rotation period and per track of the specimen analysis disc 200 according to the reference-position detection signal KS output from the reference-position detection sensor 6. The controller 9 defines the reaction regions 210 based on the reference position detected.

The storage unit 10 stores measurement parameters SP1 for every track in each reaction region 210. The measurement parameters SP1 include measurement information such as the number of the reaction regions 210, the time corresponding to the distance from the slit 202 as a reference-position defining portion to each reaction region 210, and the timing of the measurement gate signals of each track.

The controller 9 reads the measurement parameters SP1 from the storage unit 10, and sequentially generates measurement gate signals GS1 for the respective tracks in each reaction region 210 based on the measurement parameters SP1. The controller 9 extracts a fine particle pulse signal BS per measurement gate signal GS1 from the reception level signal JS output from the optical pickup 20. The method of generating the measurement gate signals GS1 and extracting the fine particle pulse signal BS will be described below.

The controller 9 counts the number of the fine particles 131 labeling the detection target substances 121 from the extracted fine particle pulse signal BS. The controller 9 directs the storage unit 10 to store the number of the fine particles 131 per measurement gate signal GS1 in each reaction region 210. The controller 9 adds up the number of the fine particles 131 in each reaction region 210 and displays the sum on the display unit 11. The number of the fine particles 131 displayed corresponds to the number of the detection target substances 121. The method of defining the bubble region included in each reaction region 210 and the method of correcting the result of the measured fine particles 131 in the bubble region will be described below.

The analysis method of analyzing the detection target substances 121 by the analysis device 1, more particularly, the method of analyzing the fine particles 131 labeling the detection target substances 121, is described below with reference to FIG. 9 to FIG. 13.

Figure 9:
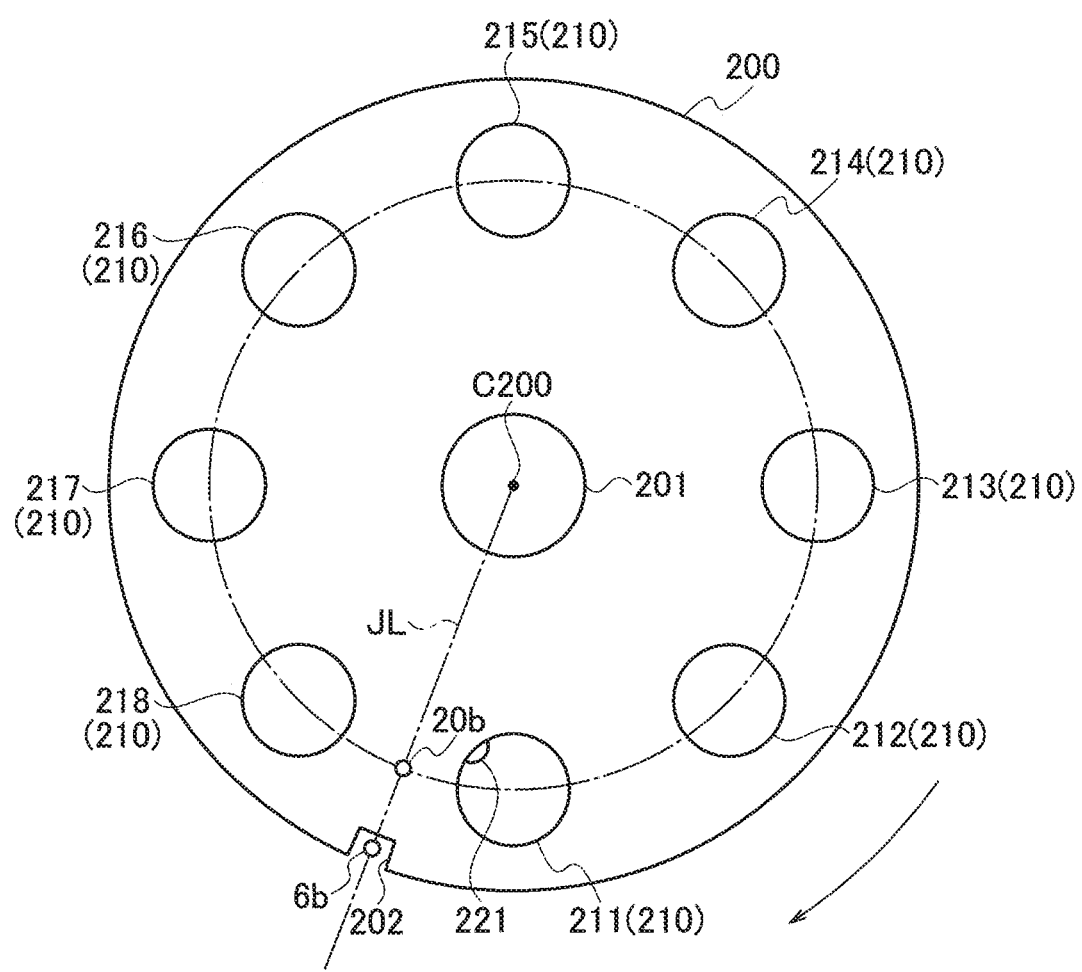
FIG. 9 is a plan view for describing a positional relationship between detection positions of a reference-position detection sensor and an optical pickup, and positions of a slit and reaction regions on the disc for specimen analysis.

FIG. 9 schematically illustrates a positional relationship between the detection positions of the reference-position detection sensor 6 and the optical pickup 20, and the positions of the slit 202 and the respective reaction regions 210 in the specimen analysis disc 200. The arrow in FIG. 9 indicates the rotation direction of the specimen analysis disc 200. Reference sign 6b indicates the detection position of the reference-position detection sensor 6. The axial line JL corresponds to the guide shaft 7.

The detection position 6b of the reference-position detection sensor 6 is located on the axial line JL, in FIG. 9, but is not limited to this illustration. The detection position 6b may be any position at which the slit 202 can be detected at the circumferential edge of the specimen analysis disc 200. The optical pickup 20 moves along the axial line JL in the radial direction of the specimen analysis disc 200. Reference sign 20b in FIG. 9 indicates the detection position of the optical pickup 20.

Figure 10:
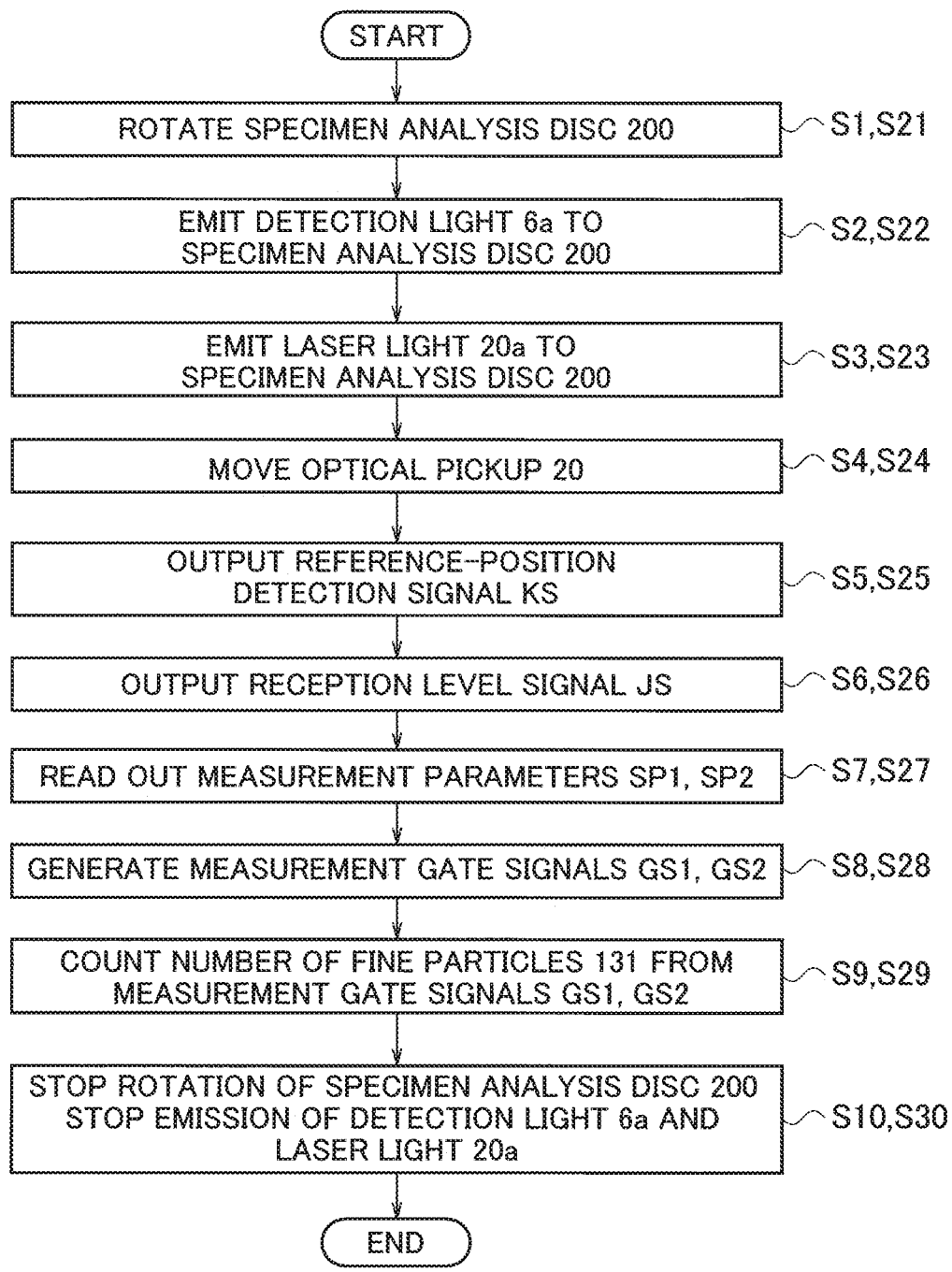
FIG. 10 is a flow chart for describing a method of analyzing the fine particles by the analysis device according to the first and second embodiments.

In step S1 in the flowchart shown in FIG. 10, the controller 9 controls the turntable drive circuit 5 to direct the turntable drive unit 4 to turn the turntable 2, so that the specimen analysis disc 200 rotates at a constant linear velocity.

In step S2, the controller 9 directs the reference-position detection sensor 6 to emit the detection light 6a to the specimen analysis disc 200. In step S3, the controller 9 directs the optical pickup 20 to emit the laser light 20a to the specimen analysis disc 200. Step S3 is not necessarily performed after step S2. Step S2 may be performed after step S3, or step S2 and step S3 may be performed simultaneously.

As shown in FIG. 9, the reaction regions 210 are arranged at regular intervals such that the respective center points are located on the common circle having the center C200 of the specimen analysis disc 200. For distinguishing the respective reaction regions 210, the reaction region to which the laser light 20a is radiated first after the reference-position detection sensor 6 detects the slit 202 with the detection light 6a is indicated by reference numeral 211, and the following reaction regions to which the laser light 20a is sequentially radiated, are indicated by reference numerals 212, 213, 214, 215, 216, 217, and 218.

Figure 11:
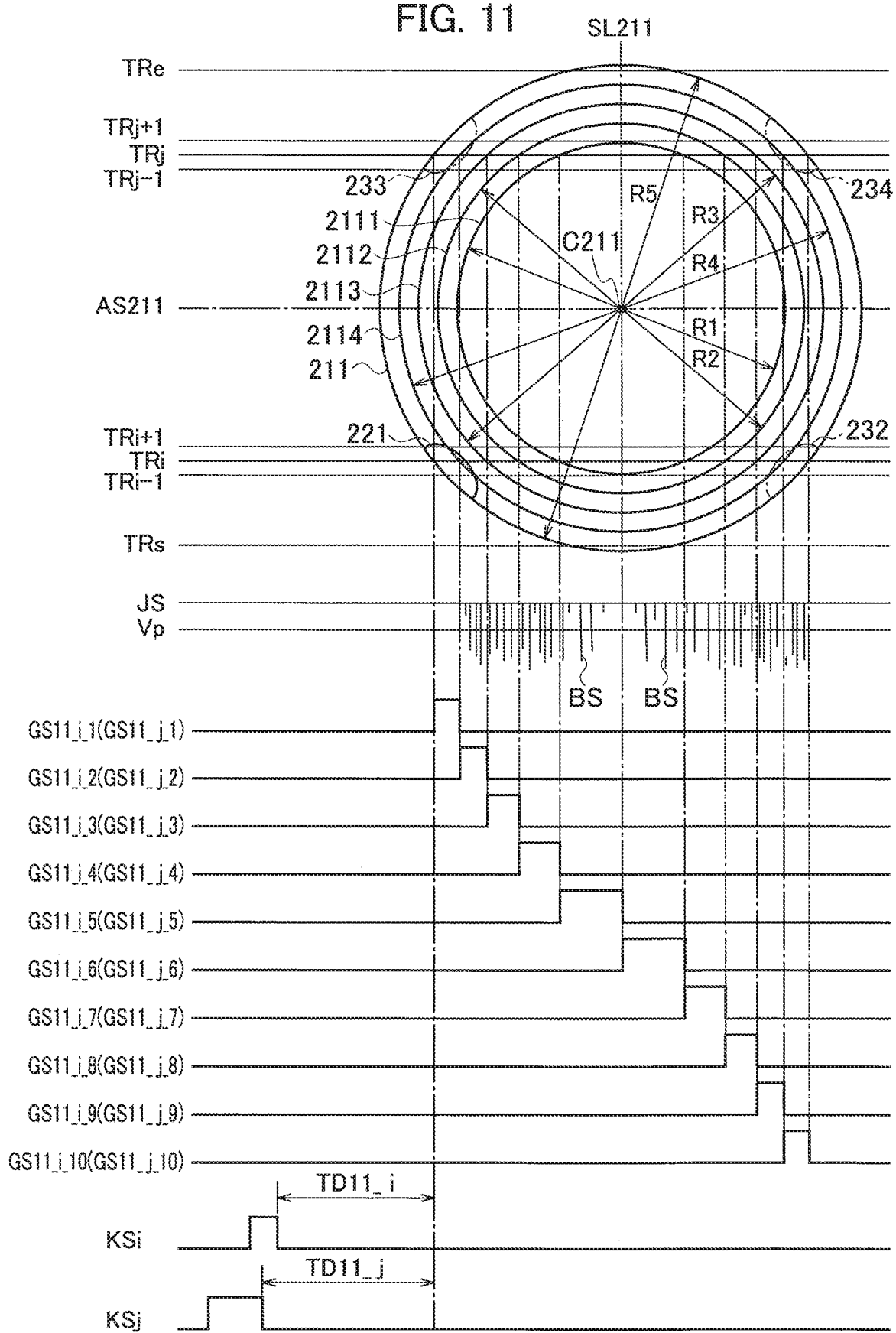
FIG. 11 is a time chart showing a relationship between the reaction region and the measurement gate signals in the method of analyzing the fine particles by the analysis device according to the first embodiment.

FIG. 11 illustrates the reaction region 211 to which the laser light 20a is radiated first after the reference-position detection sensor 6 detects the slit 202. The laser light 20a is radiated to the respective reaction regions 211 to 218 per track from the track TRs located on the inner side of the specimen analysis disc 200 to the track TRe located on the outer side of the specimen analysis disc 200.

FIG. 11 illustrates a state in which a bubble region 221 is formed across the tracks TRi−1, TRi, and TRi+1 in the reaction region 211. The bubble region 221 is formed such that the bubbles 113, the bubbles 123, or the bubbles 133 adhere to the track region 205 of the specimen analysis disc 200 in step S101, step S102, or step S103 shown in FIG. 4. The respective tracks TRs, TRi−1, TRi, TRi+1, TRj−1, TRj, TRj+1, and TRe are indicated by straight lines in FIG. 11 for illustration purposes.

The process in which the track TRi in the reaction region 211 including the bubble region 221 is scanned with the laser light 20a is described below.

In step S4, the controller 9 controls the optical pickup drive circuit 8 to move the optical pickup 20 so that the laser light 20a is radiated to the track TRi of the specimen analysis disc 200. In step S5, the reference-position detection sensor 6 detects the slit 202 to generate the reference-position detection signal KS, and outputs the signal to the controller 9.

In step S6, the optical pickup 20 receives the reflected light from the specimen analysis disc 200. The optical pickup 20 detects the reception level of the reflected light, generates the reception level signal JS, and outputs the signal to the controller 9.

For distinguishing the reference-position detection signals KS in the respective tracks, the reference-position detection signal in the track TRi is indicated by reference sign KSi, and the reference-position detection signal in the track TRj is indicated by reference sign KSj. For distinguishing the measurement parameters SP1 in the respective tracks TR in each reaction region 210, the measurement parameter in the track TRi is indicated by reference sign SP11_i, and the measurement parameter in the track TRj is indicated by reference sign SP11_j in the reaction region 211.

In step S7, the controller 9 detects the reference-position detection signal KSi, and reads out the measurement parameter SP11_i of the track TRi in the reaction region 211 from the storage unit 10.

In step S8, based on the measurement parameter SP11_i, the controller 9 generates measurement gate signals GS11_i_1, GS11_i_2, GS11_i_3, GS11_i_4, GS11_i_5, GS11_i_6, GS11_i_7, GS11_i_8, GS11_i_9, and GS11_i_10, which are pulse signals for measuring the fine particles 131 in the track TRi per section in the reaction region 211.

The measurement parameter SP11_i includes measurement information such as the number of the measurement gate signals GS1 in the track TRi in the reaction region 211, the time TD11_i from the fall of the reference-position detection signal KSi to the rise of the first measurement gate signal GS11_i_1, and each pulse width of the measurement gate signals GS11_i_1 to GS11_i_10. The controller 9 generates the measurement gate signal GS11_i_1, which rises after the time TD11_i has passed since the fall of the reference-position detection signal KSi, and sequentially generates the following measurement gate signals GS11_i_2 to GS11_i_10.

The measurement gate signals GS11_i_1 to GS11_i_10 are generated at the timing when the reaction region 211 is divided into {(2×n)+2} sections in the track TRi by the n-number (n=4 in this case) concentric circles 2111, 2112, 2113, and 2114, having the center C211 of the reaction region 211, and by the dividing line SL211 passing through the center C200 of the specimen analysis disc 200 and the center C211 of the reaction region 211. For example, as shown in FIG. 11, when the diameters of the concentric circles 2111, 2112, 2113, and 2114 are defined as R1, R2, R3, and R4, and the diameter of the reaction region 210 is defined as R5, the relationship of R1<R2<R3<R4<R5 is fulfilled.

Figure 4:
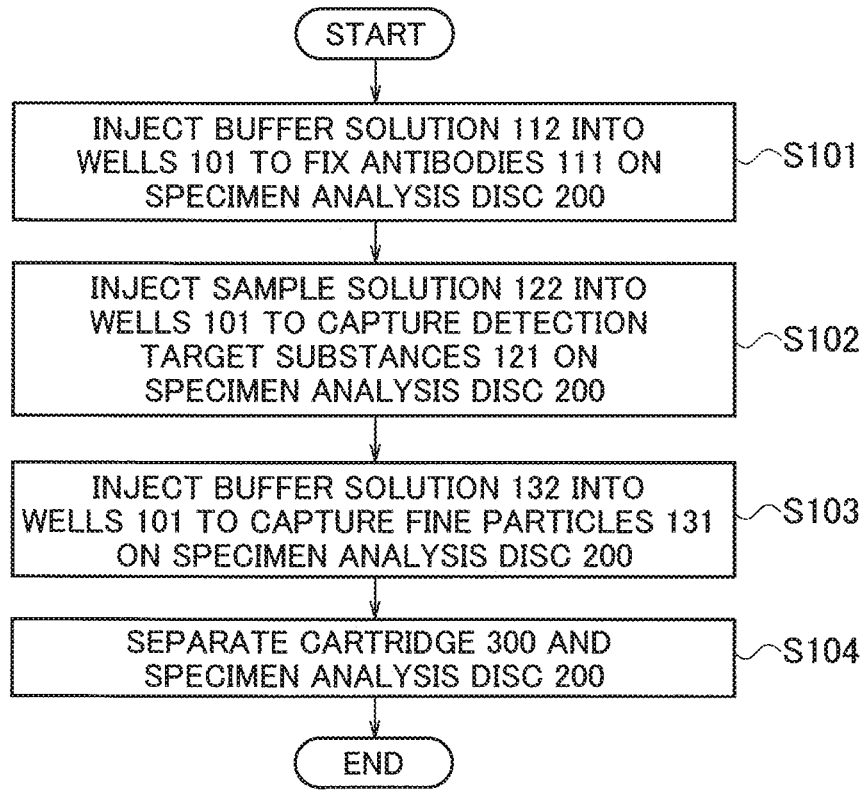
FIG. 4 is a flow chart for describing a method of forming a reaction region on the disc for specimen analysis.

In step S101, step S102, or step S103 shown in FIG. 4, the bubbles 113, the bubbles 123, or the bubbles 133 tend to adhere to the boundary between the inner surface and the bottom of the wells 101, namely, the boundary between the inner surface of the insertion holes 301 of the cartridge 300 and the track region 205 of the specimen analysis disc 200, as described above. The bubble region thus tends to be formed on the circumferential side of each reaction region 210. The respective measurement parameters SP1 are therefore preferably set such that the concentric circles 2111, 2112, 2113, and 2114 are located toward the outer circumference of each reaction region 210.

When n=4, the measurement parameter SP11_i is set such that ten measurement gate signals GS1 are generated in the track TRi to the track TRj, eight measurement gate signals GS1 are generated in the track TRi−1 and the track TRj+1, and two measurement gate signals GS1 are generated in the track TRs and the track TRe.

In step S9, the controller 9 extracts the fine particle pulse signal BS from the reception level signal JS output from the optical pickup 20 in the period from the rise to the fall of the measurement gate signal GS11_i_1 (corresponding to the pulse width), and counts and stores the number of the fine particles 131 in the storage unit 10. The controller 9 extracts the fine particle pulse signal BS from the reception level signal JS output from the optical pickup 20 in the period from the rise to the fall of each of the measurement gate signal GS11_i_2 to the measurement gate signal GS11_i_10, and counts the number of the fine particles 131 and stores the results of the measured fine particles 131 in the storage unit 10.

The reception level signal JS may include noise other than the fine particle pulse signal BS. The controller 9 thus compares the pulse signal included in the reception level signal JS with the threshold Vp so as to define the pulse signal less than or equal to the threshold Vp as the fine particle pulse signal BS.

The controller 9 counts the number of the fine particles 131 per measurement gate signal GS1 in the all tracks TR from the track TRs to the track TRe of each reaction region 210 from the reaction regions 211 to 218, and stores the results of the measured fine particles 131 in the storage unit 10.

In step S10, the controller 9 controls the turntable drive circuit 5 to stop the rotation of the specimen analysis disc 200. The controller 9 controls the reference-position detection sensor 6 and the optical pickup 20 to stop the emission of the detection light 6a and the laser light 20a.

The method of defining the bubble region 221 and the method of correcting the result of the measured fine particles 131 in the bubble region 221 by the analysis device 1 are described below, with reference to FIG. 11 to FIG. 13.

The method of defining the bubble region 221 and the method of correcting the result of the measured fine particles 131 in the bubble region 221 by the analysis device 1 are described below in the case in which the bubble region 221 is formed across the tracks TRi−1, TRi, and TRi+1 in the reaction region 211, as shown in FIG. 11.

Since the fine particles 131 are not captured on the track region 205 in the bubble region 221, the fine particle pulse signal BS is not detected in the bubble region 221. For example, the fine particle pulse signal BS is not detected in the period from the rise to the fall of the measurement gate signal GS11_i_1 corresponding to the measurement position of the bubble region 221 in the track TRi.

Figure 12:
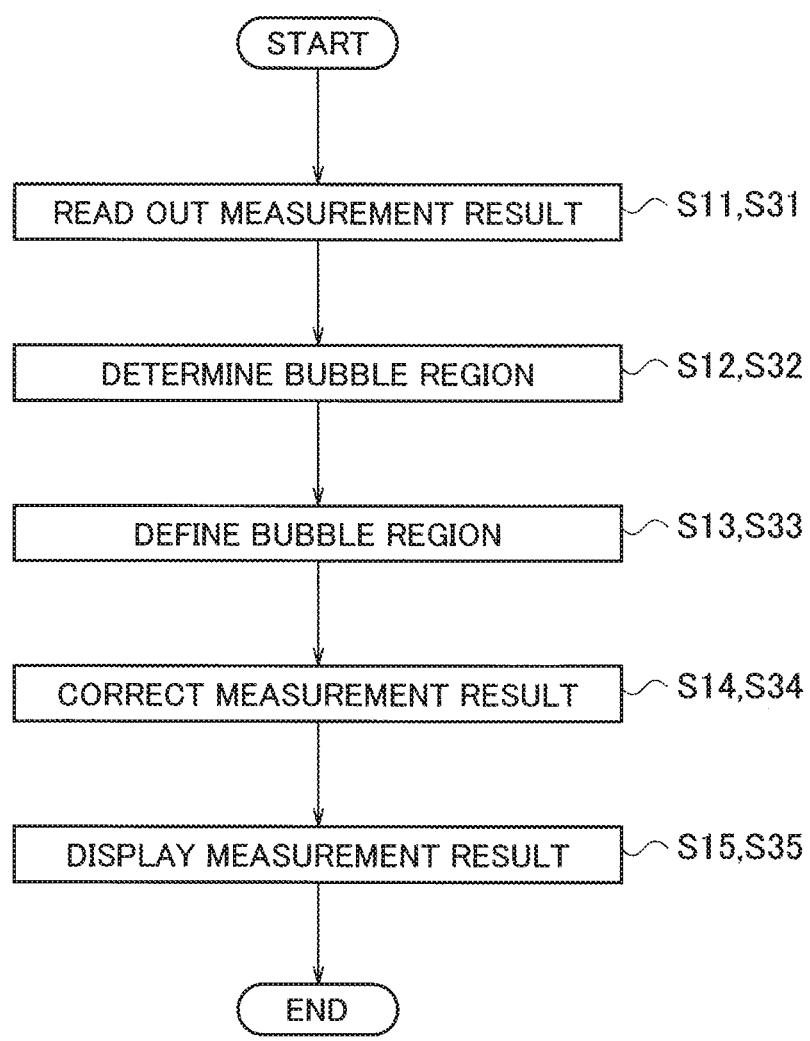
FIG. 12 is a flow chart for describing a method of defining a bubble region and a method of correcting a result of measured fine particles in the bubble region by the analysis device according to the first and second embodiments.
Figure 13:
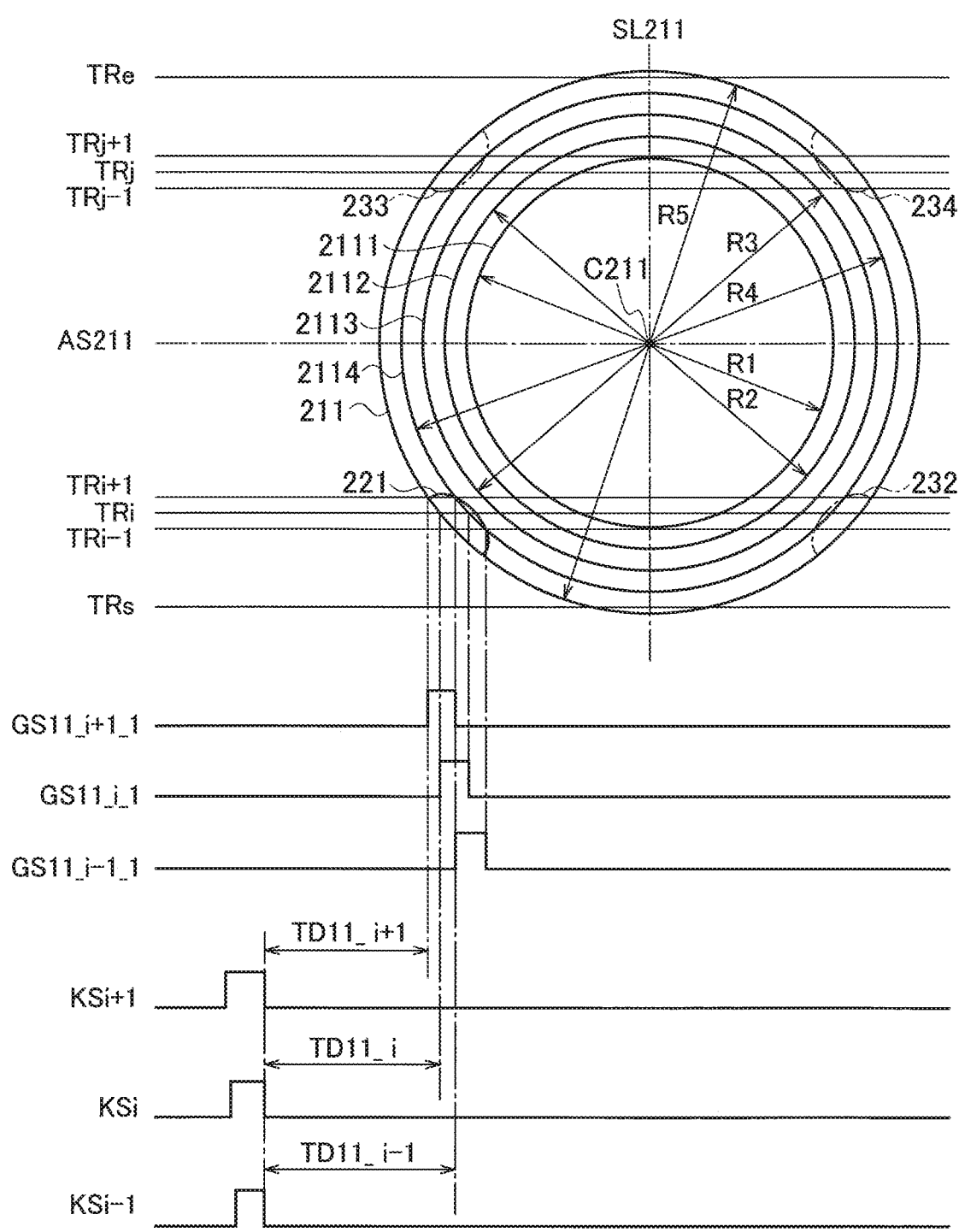
FIG. 13 is a time chart showing a relationship between tracks adjacent to each other and the measurement gate signals in the method of analyzing the fine particles by the analysis device according to the first embodiment.

In step S11 in the flow chart shown in FIG. 12, the controller 9 reads out the measurement results obtained from the respective measurement gate signals GS1 in each reaction region 210 from the storage unit 10. For example, the controller 9 reads out the results of the measured fine particles 131 for the respective measurement gate signals GS1 in the reaction region 211.

In step S12, the controller 9 compares the measurement results obtained at the positions having a symmetric relation with each other in each reaction region 210. The following is the case of comparing the measurement result obtained from the measurement gate signal GS11_i_1 in the track TRi with the measurement results obtained from the other measurement gate signals GS1 at the positions having a symmetric relation with the measurement gate signal GS11_i_1.

The measurement gate signal GS11_i_1 (the first measurement gate signal) has a symmetric relation regarding the measurement position with the measurement gate signal GS11_i_10 (the second measurement gate signal) about the dividing line SL211, and has the same pulse width as the measurement gate signal GS11_i_10. The measurement gate signal GS11_i_1 has the same distance from the center C211 of the reaction region 211 regarding the measurement position as the measurement gate signal GS11_i_10. Thus, the measurement result obtained from the measurement gate signal GS11_i_1 has a symmetric positional relation with the measurement result obtained from the measurement gate signal GS11_i_10 about the dividing line SL211.

The track TRi has a symmetric positional relation with the track TRj about the symmetric axis AS211 passing through the center C211 of the reaction region 211 and perpendicular to the dividing line SL211. Based on the measurement parameter SP11_j, the controller 9 generates the measurement gate signals GS11_j_1, GS11_j_2, GS11_j_3, GS11_j_4, GS11_j_5, GS11_j_6, GS11_j_7, GS11_j_8, GS11_j_9, and GS11_j_10, which are pulse signals for measuring the fine particles 131 in the track TRj per section in the reaction region 211. The controller 9 generates the measurement gate signal GS11_j_1, which rises after the time TD11_j has passed since the fall of the reference-position detection signal KSj, and sequentially generates the following measurement gate signals GS11_j_2 to GS11_j_10.

The measurement gate signal GS11_i_1 has a symmetric relation regarding the measurement position with the measurement gate signal GS11_j_1 (the third measurement gate signal) about the symmetric axis AS211, and has the same pulse width as the measurement gate signal GS11_j_1. The measurement gate signal GS11_i_1 has the same distance from the center C211 of the reaction region 211 regarding the measurement position as the measurement gate signal GS11_j_1. Thus, the measurement result obtained from the measurement gate signal GS11_i_1 has a symmetric positional relation with the measurement result obtained from the measurement gate signal GS11_j_1 about the symmetric axis AS211.

Similarly, the measurement gate signal GS11_i_10 has a symmetric relation regarding the measurement position with the measurement gate signal GS11_j_10 (the fourth measurement gate signal) about the symmetric axis AS211, and has the same pulse width as the measurement gate signal GS11_j_10. The measurement gate signal GS11_i_10 has the same distance from the center C211 of the reaction region 211 regarding the measurement position as the measurement gate signal GS11_j_10. Thus, the measurement result obtained from the measurement gate signal GS11_i_10 has a symmetric positional relation with the measurement result obtained from the measurement gate signal GS11_j_10 about the symmetric axis AS211.

Therefore, the respective measurement results obtained from the measurement gate signal GS11_i_1, the measurement gate signal GS11_i_10, the measurement gate signal GS11_j_1, and the measurement gate signal GS11_j_10 have a symmetric positional relation with each other. The controller 9 compares the respective measurement results obtained from the measurement gate signal GS11_i_1, the measurement gate signal GS11_i_10, the measurement gate signal GS11_j_1 and the measurement gate signal GS11_j_10.

More particularly, the controller 9 calculates the average of the number of the fine particles 131 obtained from the measurement gate signal GS11_i_1, the measurement gate signal GS11_i_10, the measurement gate signal GS11_j_1, and the measurement gate signal GS11_j_10. The number of the fine particles 131 obtained from each of the measurement gate signal GS11_i_1, the measurement gate signal GS11_i_10, the measurement gate signal GS11_j_1, and the measurement gate signal GS11_j_10 is in general substantially the same when the bubble region 221 is not formed.

The controller determines whether or not the region corresponding to the measurement gate signal GS1, in which the number of the fine particles 131 obtained is less than or equal to a predetermined ratio to the average, is the bubble region. Since the fine particles 131 are not captured at the measurement position corresponding to the measurement gate signal GS11_i_1, the controller 9 determines whether or not the region corresponding to the measurement gate signal GS11_i_1 is the bubble region.

Since the fine particles 131 are not captured in the bubble region 221 because of the bubbles 113, 123, or 133, it is preferable to correct the measurement result in the bubble region 221. The bubble region 221 is a measurement-result-correction target region in which the number of the fine particles 131 is corrected. The number of the fine particles 131 obtained from the measurement gate signal GS1 is affected by the number of the detection target substances 121 included in the sample solution 122. The bubble region is therefore preferably determined according to not the absolute value, but the ratio of the number of the fine particles 131.

In step S13, the controller 9 compares the measurement results of the adjacent tracks TR in each reaction region 210. The bubbles 113, the bubbles 123, or the bubbles 133 adhering to the track region 205 of the specimen analysis disc 200 in step S101, step S102, or step S103, are in general formed across the several tracks TR. As shown in FIG. 13, the measurement positions of the measurement gate signal GS11_i−1_1 in the track TRi−1, the measurement gate signal GS11_i_1 in the track TRi, and the measurement gate signal GS11_i+1_1 in the track TRi+1 are continuous along the circumference of the reaction region 211. FIG. 13 corresponds to FIG. 11.

The controller 9 compares the measurement results obtained from the measurement gate signal GS11_i−1_1, the measurement gate signal GS11_i_1, and the measurement gate signal GS11_i+1_1 in the track TRi−1, the track TRi, and the track TRi+1 adjacent to each other in the reaction region 211, for example.

When it is determined that the respective regions corresponding to the measurement gate signals GS11_i−1_1, GS11_i_1, and GS11_i+1_1 are the bubble regions in step S12, the controller 9 defines the regions corresponding to the measurement gate signals GS11_i−1_1, GS11_i_1, and GS11_i+1_1 collectively as the bubble region 221 formed across the track TRi−1, the track TRi, and the track TRi+1.

In step S14, the controller 9 corrects the measurement results of the measured fine particles 131 in the bubble region 221. For example, the controller 9 calculates the average of the number of the fine particles obtained from the measurement gate signals GS11_i_10, GS11_j_1, and GS11_j_10 not defined as the bubble region 221, and corrects the number of the fine particles 131 obtained from the measurement gate signal GS11_i_1 defined as the bubble region 221 to the calculated average.

Similarly, the controller 9 calculates the average of the number of the fine particles obtained from the measurement gate signals GS11_i−1_10, GS11_j+1_1, and GS11_j+1_10, and corrects the number of the fine particles 131 obtained from the measurement gate signal GS11_i−1_1 to the calculated average. The controller 9 also calculates the average of the number of the fine particles obtained from the measurement gate signals GS11_i+1_10, GS11_j−1_1, and GS11_j−1_10, and corrects the number of the fine particles 131 obtained from the measurement gate signal GS11_i+1_1 to the calculated average.

Namely, the region 232 corresponding to the measurement gate signals GS11_i−1_10, GS11_i_10, and GS11_i+1_10, the region 233 corresponding to the measurement gate signals GS11_j−1_1, GS11_j_1, and GS11_j+1_1, and the region 234 corresponding to the measurement gate signals GS11_j−1_10, GS11_j_10 and GS11_j+1_10 are comparison target regions used for correcting the number of the fine particles 131 in the bubble region 221.

The controller 9 performs the process from step S11 to step S14 in every track TRs to TRe in each reaction region 210 (in all reaction regions 211 to 218).

In step S15, the controller 9 displays the measurement results and the correction results of the fine particles 131 in each reaction region 210 on the display unit 11.

The analysis device 1 and the analysis method according to the first embodiment can compare the measurement results obtained in the regions having a symmetric relation with each other in each reaction region, and further compare the measurement results in the adjacent tracks, so as to define the bubble region 221. The analysis device 1 and the analysis method can also correct the measurement result at the position defined as the bubble region 221, among the measurement results having a symmetric relation with each other, based on the other measurement results at the positions not defined as the bubble region.

Second Embodiment

Figure 8:
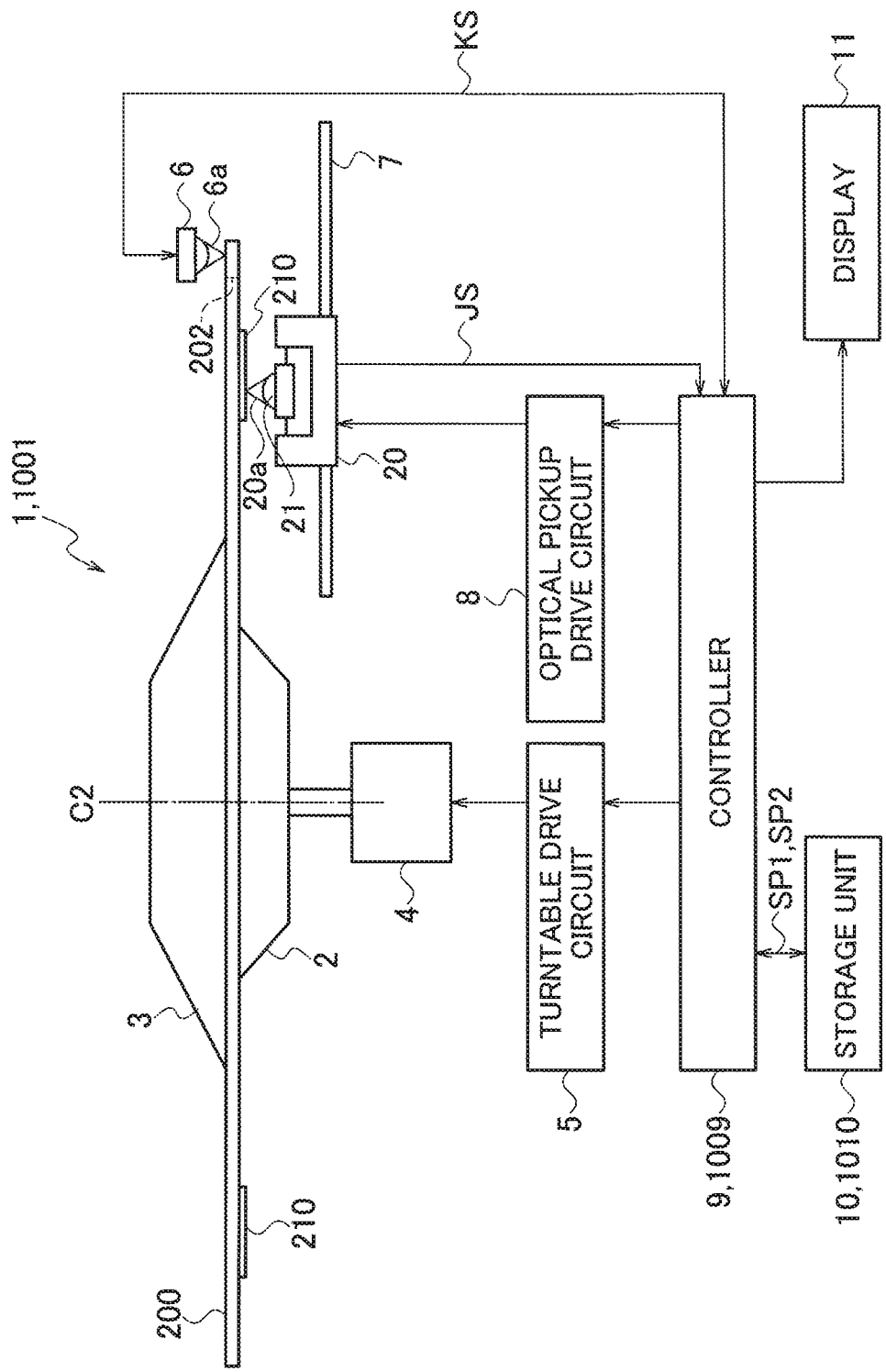
FIG. 8 is a configuration diagram showing an analysis device according to first and second embodiments.

An analysis device and an analysis method according to a second embodiment are described below with reference to FIG. 8, FIG. 10, FIG. 12, FIG. 14, and FIG. 15. As shown in FIG. 8, the analysis device 1001 according to the second embodiment includes a controller 1009 and a storage unit 1010, instead of the controller 9 and the storage unit 10, respectively. The analysis method of analyzing fine particles by the analysis device 1001 differs from the analysis method by the analysis device 1. Hereinafter, the analysis method of analyzing fine particles by the analysis device 1001 is described below. The same elements as in the analysis device 1 according to the first embodiment are denoted by the same reference numerals for illustration purposes.

When the detection target substances 121 are exosomes having a size as small as 100 nm, it is difficult to optically detect the detection target substance 121 directly. The analysis device 1001 according to the second embodiment detects and measures the fine particles 131 captured on the reaction regions 210, so as to indirectly detect and measure the detection target substances 121 specifically binding to the fine particles 131.

The controller 1009 controls the turntable drive circuit 5 and the optical pickup drive circuit 8. The controller 1009 controls the turntable drive circuit 5 to stop or rotate the turntable 2 at a constant linear velocity, for example. The controller 1009 controls the optical pickup drive circuit 8 to move the optical pickup 20 to a target position in the radial direction of the specimen analysis disc 200 or adjust the position of the objective lens 21 in the vertical direction so as to condense the laser light 20a on the track region 205. A CPU may be used as the controller 1009, for example.

The controller 1009 detects the reference position per rotation period and per track of the specimen analysis disc 200 according to the reference-position detection signal KS output from the reference-position detection sensor 6. The controller 1009 defines the reaction regions 210 based on the reference position detected.

The storage unit 1010 stores measurement parameters SP2 for every track in each reaction region 210. The measurement parameters SP2 include measurement information such as the number of the reaction regions 210, the time corresponding to the distance from the slit 202 as a reference-position defining portion to each reaction region 210, and the timing of the measurement gate signals of each track.

The controller 1009 reads the measurement parameters SP2 from the storage unit 1010, and sequentially generates measurement gate signals GS2 for the respective tracks in each reaction region 210 based on the measurement parameters SP2. The controller 1009 extracts a fine particle pulse signal BS per measurement gate signal GS2 from the reception level signal JS output from the optical pickup 20. The method of generating the measurement gate signals GS2 and extracting the fine particle pulse signal BS will be described below.

The controller 1009 counts the number of the fine particles 131 labeling the detection target substances 121 from the extracted fine particle pulse signal BS. The controller 1009 directs the storage unit 1010 to store the number of the fine particles 131 per measurement gate signal GS2 in each reaction region 210. The controller 1009 adds up the number of the fine particles 131 in each reaction region 210 and displays the sum on the display unit 11. The number of the fine particles 131 displayed corresponds to the number of the detection target substances 121. The method of defining the bubble region included in each reaction region 210 and the method of correcting the result of the measured fine particles 131 in the bubble region will be described below.

The analysis method of analyzing the detection target substances 121 by the analysis device 1001, more particularly, the method of analyzing the fine particle 131 labeling the detection target substances 121 is described with reference to FIG. 10, FIG. 12, FIG. 14, and FIG. 15.

In step S21 in the flowchart shown in FIG. 10, the controller 1009 controls the turntable drive circuit 5 to direct the turntable drive unit 4 to turn the turntable 2 so that the specimen analysis disc 200 rotates at a constant linear velocity.

In step S22, the controller 1009 directs the reference-position detection sensor 6 to emit the detection light 6a to the specimen analysis disc 200. In step S23, the controller 1009 directs the optical pickup 20 to emit the laser light 20a to the specimen analysis disc 200. Step S23 is not necessarily performed after step S22. Step S22 may be performed after step S23, or step S22 and step S23 may be performed simultaneously.

Figure 14:
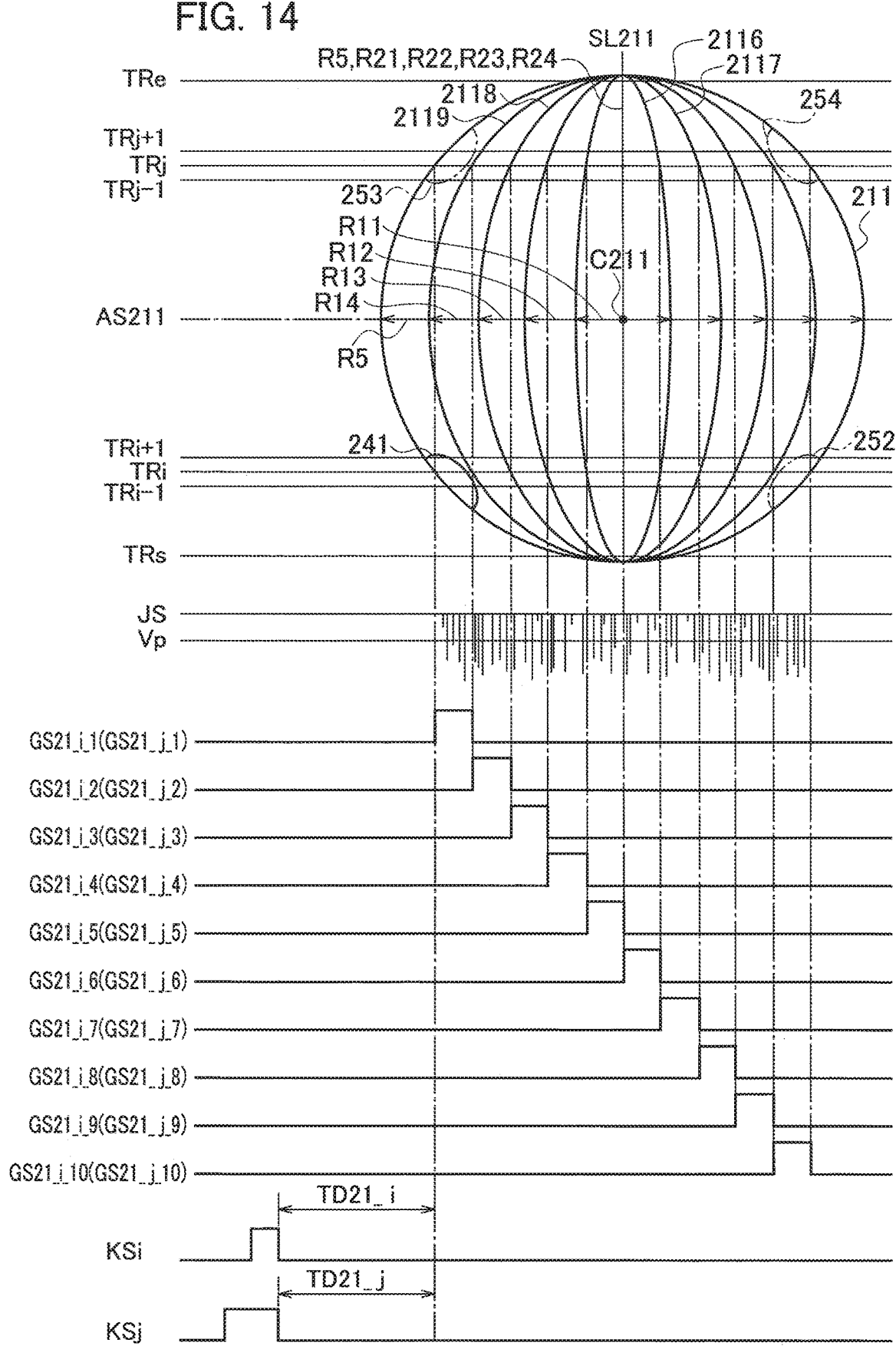
FIG. 14 is a time chart showing a relationship between the reaction region and the measurement gate signals in the method of analyzing the fine particles by the analysis device according to the second embodiment.

FIG. 14 illustrates the reaction region 211 to which the laser light 20a is radiated first after the reference-position detection sensor 6 detects the slit 202. The laser light 20a is radiated to the respective reaction regions 211 to 218 per track from the track TRs located on the inner side of the specimen analysis disc 200 to the track TRe located on the outer side of the specimen analysis disc 200.

FIG. 14 illustrates a state in which a bubble region 241 is formed across the tracks TRi−1, TRi, and TRi+1 in the reaction region 211. The bubble region 241 is formed such that the bubbles 113, the bubbles 123, or the bubbles 133 adhere to the track region 205 of the specimen analysis disc 200 in step S101, step S102, or step S103 shown in FIG. 4. The respective tracks TRs, TRi−1, TRi, TRi+1, TRj−1, TRj, TRj+1, and TRe are indicated by straight lines in FIG. 14 for illustration purposes.

The process in which the track TRi in the reaction region 211 including the bubble region 241 is scanned with the laser light 20a is described below.

In step S24, the controller 1009 controls the optical pickup drive circuit 8 to move the optical pickup 20 so that the laser light 20a is radiated to the track TRi of the specimen analysis disc 200. In step S25, the reference-position detection sensor 6 detects the slit 202 to generate the reference-position detection signal KS, and outputs the signal to the controller 1009.

In step S26, the optical pickup 20 receives the reflected light from the specimen analysis disc 200. The optical pickup 20 detects the reception level of the reflected light, generates the reception level signal JS, and outputs the signal to the controller 1009.

For distinguishing the measurement parameters SP2 in the respective tracks TR in each reaction region 210, the measurement parameter in the track TRi is indicated by reference sign SP21_i, and the measurement parameter in the track TRj is indicated by reference sign SP21_j in the reaction region 211.

In step S27, the controller 1009 detects the reference-position detection signal KSi, and reads out the measurement parameter SP21_i of the track TRi in the reaction region 211 from the storage unit 1010.

In step S28, based on the measurement parameter SP21_i, the controller 1009 generates the measurement gate signals GS21_i_1, GS21_i_2, GS21_i_3, GS21_i_4, GS21_i_5, GS21_i_6, GS21_i_7, GS21_i_8, GS21_i_9, and GS21_i_10, which are pulse signals for measuring the fine particles 131 in the track TRi per section in the reaction region 211.

The measurement parameter SP21_i includes measurement information such as the number of the measurement gate signals GS2 in the track TRi in the reaction region 211, the time TD21_i from the fall of the reference-position detection signal KSi to the rise of the first measurement gate signal GS21_i_1, and each pulse width of the measurement gate signals GS21_i_1 to GS21_i_10. The controller 1009 generates the measurement gate signal GS21_i_1, which rises after the time TD21_i has passed since the fall of the reference-position detection signal KSi, and sequentially generates the following measurement gate signals GS21_i_2 to GS21_i_10.

The measurement gate signals GS21_i_1 to GS21_i_10 are generated at the timing when the reaction region 211 is divided into {(2×n)+2} sections in each track TR by the dividing line SL211 and the n-number (n=4 in this case) ellipses 2116, 2117, 2118, and 2119 having the center C211 of the reaction region 211.

The long axis of the respective ellipses 2116, 2117, 2118, and 2119 conforms to the dividing line SL211. The ends of the long axis of the respective ellipses 2116, 2117, 2118, and 2119 are located on the outer circumference of each reaction region 210. For example, as shown in FIG. 14, when the short diameters of the ellipses 2116, 2117, 2118, and 2119 are defined as R11, R12, R13, and R14, and the long diameters of the ellipses 2116, 2117, 2118, and 2119 are defined as R21, R22, R23, and R24, the relationships of R11<R12<R13<R14<R5 and R21=R22=R23=R24=R5 are fulfilled. The ellipses 2116, 2117, 2118, and 2119 have the same long diameter and different short diameters. Thus, when n=4, ten measurement gate signals GS2 are generated in all tracks TR (TRs to TRe).

In step S101, step S102, or step S103 shown in FIG. 4, the bubbles 113, the bubbles 123, or the bubbles 133 tend to adhere to the boundary between the inner surface and the bottom of the wells 101, namely, the boundary between the inner surface of the insertion holes 301 of the cartridge 300 and the track region 205 of the specimen analysis disc 200, as described above. The bubble region thus tends to be formed on the circumferential side of the reaction regions 210. The measurement parameters SP2 are therefore preferably set such that the ends of the short axis of the restive ellipses 2116, 2117, 2118, and 2119 are located toward the outer circumference of each reaction region 210.

In step S29, the controller 1009 extracts the fine particle pulse signal BS from the reception level signal JS output from the optical pickup 20 in the period from the rise to the fall of the measurement gate signal GS21_i_1 (corresponding to the pulse width), and counts and stores the number of the fine particles 131 in the storage unit 1010. The controller 1009 extracts the fine particle pulse signal BS from the reception level signal JS output from the optical pickup 20 in the period from the rise to the fall of each of the measurement gate signal GS21_i_2 to the measurement gate signal GS21_i_10, counts the number of the fine particles 131, and stores the results of the measured fine particles 131 in the storage unit 1010.

The reception level signal JS may include noise other than the fine particle pulse signal BS. The controller 1009 thus compares the pulse signal included in the reception level signal JS with the threshold Vp so as to define the pulse signal less than or equal to the threshold Vp as the fine particle pulse signal BS.

The controller 1009 counts the number of the fine particles 131 per measurement gate signal GS2 in all tracks from the track TRs to the track TRe of each reaction region 210 from the reaction regions 211 to 218, and stores the results of the measured fine particles in the storage unit 1010.

In step S30, the controller 1009 controls the turntable drive circuit 5 to stop the rotation of the specimen analysis disc 200. The controller 1009 controls the reference-position detection sensor 6 and the optical pickup 20 to stop the emission of the detection light 6a and the laser light 20a.

Figure 15:
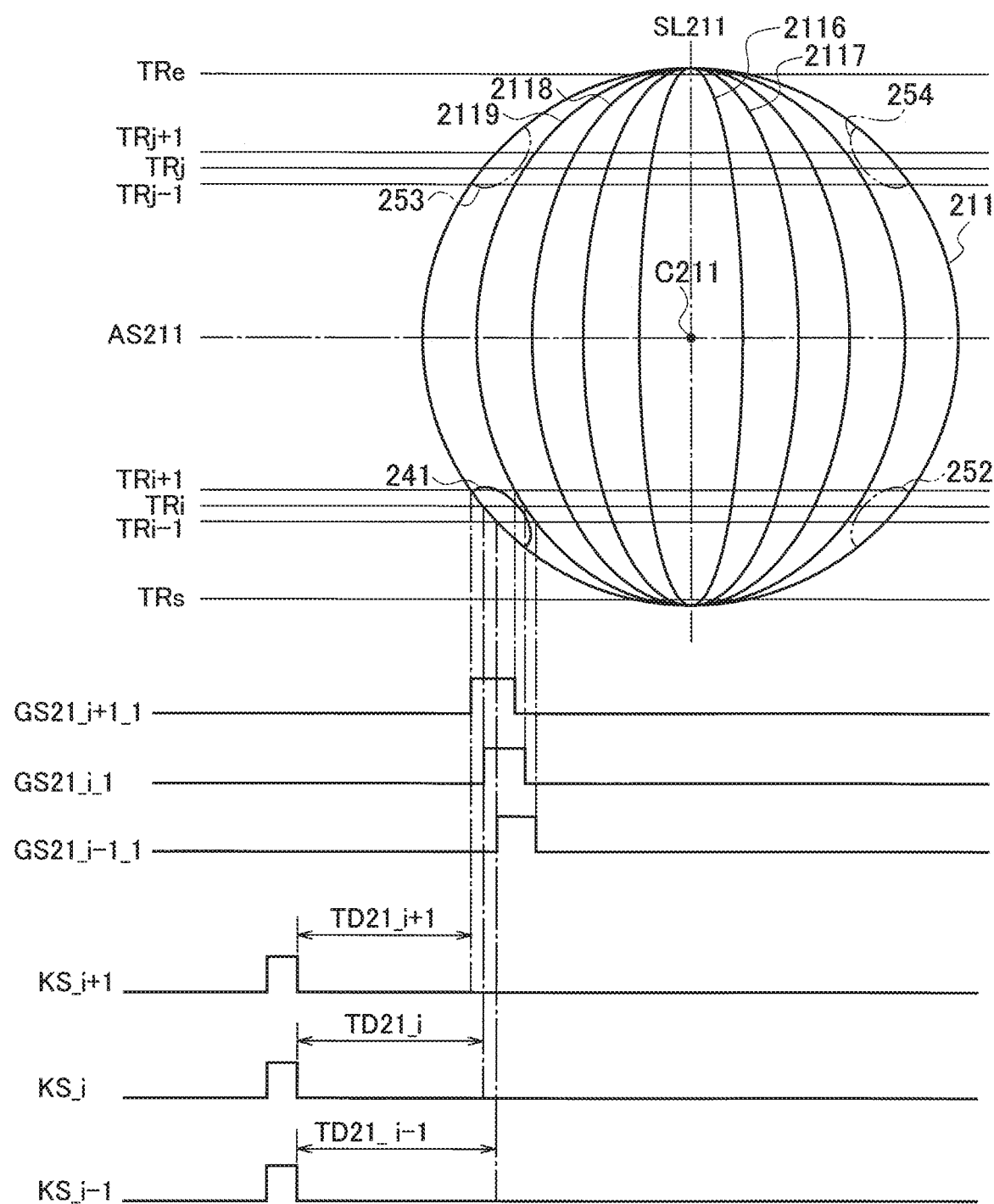
FIG. 15 is a time chart showing a relationship between tracks adjacent to each other and the measurement gate signals in the method of analyzing the fine particles by the analysis device according to the second embodiment.

The method of defining the bubble region 241 and the method of correcting the result of the measured fine particles 131 in the bubble region 241 by the analysis device 1001 are described below with reference to FIG. 12, FIG. 14, and FIG. 15.

The method of defining the bubble region 241 and the method of correcting the result of the measured fine particles 131 in the bubble region 241 by the analysis device 1001 are described below in the case in which the bubble region 241 is formed across the tracks TRi−1, TRi, and TRi+1 in the reaction region 211, as shown in FIG. 14.

Since the fine particles 131 are not captured on the track region 205 in the bubble region 241, the fine particle pulse signal BS is not detected in the bubble region 241. For example, the fine particle pulse signal BS is not detected in the period from the rise to the fall of the measurement gate signal GS21_i_1 corresponding to the measurement position of the bubble region 241 in the track TRi.

In step S31 in the flow chart shown in FIG. 12, the controller 1009 reads out the measurement results obtained from the respective measurement gate signals GS2 in each reaction region 210 from the storage unit 1010. For example, the controller 1009 reads out the results of the measured fine particles 131 for the respective measurement gate signals GS2 in the reaction region 211.

In step S32, the controller 1009 compares the measurement results obtained at the positions having a symmetric relation with each other in each reaction region 210. The following is the case of comparing the measurement result obtained from the measurement gate signal GS21_i_1 in the track TRi with the measurement results obtained from the other measurement gate signals GS2 at the positions having a symmetric relation with the measurement gate signal GS21_i_1.

The measurement gate signal GS21_i_1 (the fifth measurement gate signal) has a symmetric relation regarding the measurement position with the measurement gate signal GS21_i_10 (the sixth measurement gate signal) about the dividing line SL211, and has the same pulse width as the measurement gate signal GS21_i_10. The measurement gate signal GS21_i_1 has the same distance from the center C211 of the reaction region 211 regarding the measurement position as the measurement gate signal GS21_i_10. Thus, the measurement result obtained from the measurement gate signal GS21_i_1 has a symmetric positional relation with the measurement result obtained from the measurement gate signal GS21_i_10 about the dividing line SL211.

The track TRi has a symmetric positional relation with the track TRj about the symmetric axis AS211 passing through the center C211 of the reaction region 211 and perpendicular to the dividing line SL211. Based on the measurement parameter SP21_j, the controller 1009 generates the measurement gate signals GS21_j_1, GS21_j_2, GS21_j_3, GS21_j_4, GS21_j_5, GS21_j_6, GS21_j_7, GS21_j_8, GS21_j_9, GS21_j_10, which are pulse signals for measuring the fine particles 131 in the track TRj per section in the reaction region 211. The controller 1009 generates the measurement gate signal GS21_j_1, which rises after the time TD21_j has passed since the fall of the reference-position detection signal KSj, and sequentially generates the following measurement gate signals GS21_j_2 to GS21_j_10.

The measurement gate signal GS21_i_1 has a symmetric relation regarding the measurement position with the measurement gate signal GS21_j_1 (the seventh measurement gate signal) about the symmetric axis AS211, and has the same pulse width as the measurement gate signal GS21_j_1. The measurement gate signal GS21_i_1 has the same distance from the center C211 of the reaction region 211 regarding the measurement position as the measurement gate signal GS21_j_1. Thus, the measurement result obtained from the measurement gate signal GS21_i_1 has a symmetric positional relation with the measurement result obtained from the measurement gate signal GS21_j_1 about the symmetric axis AS211.

Similarly, the measurement gate signal GS21_i_10 has a symmetric relation regarding the measurement position with the measurement gate signal GS21_j_10 (the eighth measurement gate signal) about the symmetric axis AS211, and has the same pulse width as the measurement gate signal GS21_j_10. The measurement gate signal GS21_i_10 has the same distance from the center C211 of the reaction region 211 regarding the measurement position as the measurement gate signal GS21_j_10. Thus, the measurement result obtained from the measurement gate signal GS21_i_10 has a symmetric positional relation with the measurement result obtained from the measurement gate signal GS21_j_10 about the symmetric axis AS211.

Therefore, the respective measurement results obtained from the measurement gate signal GS21_i_1, the measurement gate signal GS21_i_10, the measurement gate signal GS21_j_1, and the measurement gate signal GS21_j_10 have a symmetric positional relation with each other. The controller 1009 compares the respective measurement results obtained from the measurement gate signal GS21_i_1, the measurement gate signal GS21_i_10, the measurement gate signal GS21_j_1, and the measurement gate signal GS21_j_10.

More particularly, the controller 1009 calculates the average of the number of the fine particles 131 obtained from the measurement gate signal GS21_i_1, the measurement gate signal GS21_i_10, the measurement gate signal GS21_j_1, and the measurement gate signal GS21_j_10. The number of the fine particles 131 obtained from each of the measurement gate signal GS21_i_1, the measurement gate signal GS21_i_10, the measurement gate signal GS21_j_1, and the measurement gate signal GS21_j_10 is in general substantially the same when the bubble region 241 is not formed.

The controller 1009 determines whether or not the region corresponding to the measurement gate signal GS2, in which the number of the fine particles 131 obtained is less than or equal to a predetermined ratio to the average, is the bubble region. Since the fine particles 131 are not captured at the measurement position corresponding to the measurement gate signal GS21_i_1, the controller 1009 determines whether or not the region corresponding to the measurement gate signal GS21_i_1 is the bubble region.

Since the fine particles 131 are not captured in the bubble region 241 because of the bubbles 113, 123, or 133, it is preferable to correct the measurement result in the bubble region 241. The bubble region 241 is a measurement-result-correction target region in which the number of the fine particles 131 is corrected. The number of the fine particles 131 obtained from the measurement gate signal GS2 is affected by the number of the detection target substances 121 included in the sample solution 122. The bubble region is therefore preferably determined according to not the absolute value, but the ratio of the number of the fine particles 131.

In step S33, the controller 1009 compares the measurement results of the adjacent tracks TR in each reaction region 210. The bubbles 113, the bubbles 123, or the bubbles 133 adhering to the track region 205 of the specimen analysis disc 200 in step S101, step S102, or step S103 are in general formed across the several tracks TR. As shown in FIG. 15, the measurement positions of the measurement gate signal GS21_i−1_1 in the track TRi−1, the measurement gate signal GS21_i_1 in the track TRi, and the measurement gate signal GS21_i+1_1 in the track TRi+1 are continuous along the circumference of the reaction region 211. FIG. 15 corresponds to FIG. 14.

The controller 1009 compares the measurement results obtained from the measurement gate signal GS21_i−1_1, the measurement gate signal GS21_i_1, and the measurement gate signal GS21_i+1_1 in the track TRi−1, the track TRi, and the track TRi+1 adjacent to each other in the reaction region 211, for example.

When it is determined that the respective regions corresponding to the measurement gate signals GS21_i−1_1, GS21_i_1, and GS21_i+1_1 are the bubble regions in step S32, the controller 1009 defines the regions corresponding to the measurement gate signals GS21_i−1_1, GS21_i_1, and GS21_i+1_1 collectively as the bubble region 241 formed across the track TRi−1, the track TRi, and the track TRi+1.

In step S34, the controller 1009 corrects the measurement results of the measured fine particles 131 in the bubble region 241. For example, the controller 1009 calculates the average of the number of the fine particles obtained from the measurement gate signals GS21_i_10, GS21_j_1, and GS21_j_10 not defined as the bubble region 241, and corrects the number of the fine particles 131 obtained from the measurement gate signal GS21_i_1 defined as the bubble region 241 to the calculated average.

Similarly, the controller 1009 calculates the average of the number of the fine particles obtained from the measurement gate signals GS21_i−1_10, GS21_j+1_1, and GS21_j+1_10, and corrects the number of the fine particles 131 obtained from the measurement gate signal GS21_i−1_1 to the calculated average. The controller 1009 also calculates the average of the number of the fine particles obtained from the measurement gate signals GS21_i+1_10, GS21_j−1_1, and GS21_j−1_10, and corrects the number of the fine particles 131 obtained from the measurement gate signal GS21_i+1_1 to the calculated average.

Namely, the region 252 corresponding to the measurement gate signals GS21_i−1_10, GS21_i_10, and GS21_i+1_10, the region 253 corresponding to the measurement gate signals GS21_j−1_1, GS21_j_1, and GS21_j+1_1, and the region 254 corresponding to the measurement gate signals GS21_j−1_10, GS21_j_10, and GS21_j+1_10 are comparison target regions used for correcting the number of the fine particles 131 in the bubble region 241.

The controller 1009 performs the process from step S31 to step S34 in every track TRs to TRe in each reaction region 210 (in all reaction regions 211 to 218).

In step S35, the controller 1009 displays the measurement results and the correction results of the fine particles 131 in each reaction region 210 on the display unit 11.

The analysis device 1001 and the analysis method according to the second embodiment can compare the measurement results obtained in the regions having a symmetric relation with each other in each reaction region, and further compare the measurement results in the adjacent tracks, so as to define the bubble region 241. The analysis device 1001 and the analysis method can also correct the measurement result at the position defined as the bubble region 241, among the measurement results having a symmetric relation with each other, based on the other measurement results at the positions not defined as the bubble region.

While the number of the measurement gate signals GS varies depending on the tracks TR in the analysis device 1 according to the first embodiment, the number of the measurement gate signals GS is constant in the all tracks TR in the analysis device 1001 according to the second embodiment. The accuracy of measurement and the accuracy of correction of the fine particles 131 may decrease in the track TR in which the number of the measurement gate signals GS decreases. The number of the measurement gate signals GS is therefore preferably the same in the all tracks TR.

It should be understood that the present invention is not intended to be limited to the embodiments described above, and various modifications will be apparent to those skilled in the art without departing from the scope of the present invention.

For example, instead of the case in which the measurement results are compared with each other in the all tracks adjacent to each other in step S13 or step S33, the track determined as the bubble region in step S12 or step S32 may be compared with the track adjacent to the corresponding track.

The number of concentric circles for generating the measurement gate signals GS1 and the diameter of the respective concentric circles are not limited to those described in the first embodiment and may be set at any value.

For example, the measurement parameters SP1 may be determined such that the concentric circles 2111 to 2114 have regular intervals with respect to the reaction region 210, such as (R2−R1)=(R3−R2)=(R4−R3)=(R5−R4). Alternatively, the measurement parameters SP1 may be determined such that the concentric circles 2111 to 2114 have intervals gradually decreased toward the outer circumference of the reaction region 210, such as (R2−R1)>(R3−R2)>(R4−R3)>(R5−R4), in order to improve the determination accuracy (resolution) of the bubble region formed on the circumference side of the reaction region 210.

The number of ellipses for generating the measurement gate signals GS2 and the short diameters of the ellipses are not limited to those described in the second embodiment and may be set at any value.

What is claimed is:

1. An analysis device comprising:
a turntable holding a specimen analysis disc, the specimen analysis disc having a reaction region on which fine particles binding to substances to be detected are captured on tracks, the specimen analysis disc being provided with projections and recesses alternately arranged in a radial direction, and the recesses defining the tracks and tracks;
a turntable drive unit comprising a motor which is configured to rotate the turntable;
a turntable drive circuit that controls the turntable drive unit;
an optical pickup comprising a laser light source for emitting laser light to the reaction region, an objective lens for condensing the laser light emitted from the laser light source, a receiver for receiving a reflected light from the reaction region, and a generator for generating a reception level signal of the reflected light, the optical pickup being driven in a direction perpendicular to a rotation axis of the turntable;
an optical pickup drive circuit that controls an operation of the optical pickup; and
a controller comprising a processor that controls the turntable drive circuit and the optical pickup drive circuit, wherein
the controller has a configuration to:
sequentially generate a plurality of measurement gate signals per track for counting a number of the fine particles captured on the reaction region,
count the number of the fine particles per measurement gate signal from the reception level signal,
obtain a first, a second, a third, and a fourth measurement result from a first, a second, a third, and a fourth measurement gate signal, respectively, measurement positions of the first and the third measurement gate signals having a symmetric relation with measurement positions of the second and the fourth measurement gate signals with respect to a dividing line passing through a center of the specimen analysis disc and a center of the reaction region, and measurement positions of the first and the second measurement gate signals having a symmetric relation with measurement positions of the third and the fourth measurement gate signals with respect to a symmetric axis passing through the center of the reaction region and perpendicular to the dividing line, compare the first, the second, the third, and the fourth measurement result to determine whether either one of the first, the second, the third, and the fourth measurement result is a measurement-result-correction target region for correcting the number of the fine particles due to a bubble region formed in the reaction region, calculate an average of the number of the fine particles of the three measurement results other than the measurement-result-correction target, in a case where either one of the first, the second, the third, and the fourth measurement result is determined as the measurement-result correction target, and correct the number of the fine particles of the measurement-result-correction target to the calculated average.

2. The analysis device according to claim 1, wherein the controller has a configuration to generate the measurement gate signals based on measurement parameters indicating timing when the reaction region is divided by a plurality of concentric circles whose centers are the center of the reaction region and the dividing line.

3. The analysis device according to claim 2, wherein the controller has a configuration to define the measurement-result-correction target region by comparing measurement results of the first measurement gate signal of the measurement gate signals, the second measurement gate signal at a measurement position having a symmetric relation with a measurement position of the first measurement gate signal about the dividing line, the third measurement gate signal at a position having a symmetric relation with the measurement position of the first measurement gate signal about the symmetric axis passing through the center point of the reaction region and perpendicular to the dividing line, and the fourth measurement gate signal at a position having a symmetric relation with the measurement position of the second measurement gate signal about the symmetric axis.

4. The analysis device according to claim 3, wherein the controller has a configuration to determine the measurement-result-correction target region by comparing measurement results of measurement gate signals of tracks adjacent to each other.

5. The analysis device according to claim 3, wherein, when it is determined that the measurement position of the first measurement gate signal is defined as the measurement-result-correction target region, the controller has a configuration to calculate an average of the number of the fine particles obtained from each of the second measurement gate signal, the third measurement gate signal, and the fourth measurement gate signal, and corrects the number of the fine particles obtained from the first measurement gate signal to the average.

6. The analysis device according to claim 1, wherein the controller has a configuration to generate the measurement gate signals at a timing when the reaction region is divided by a plurality of ellipses having a center point of the reaction region and having an identical long diameter and different short diameters and by a dividing line passing through the center of the specimen analysis disc and the center point of the reaction region.

7. The analysis device according to claim 6, wherein a long axis of the respective ellipses conforms to the dividing line, and ends of the long axis of the respective ellipses are located on an outer circumference of the reaction region.

8. The analysis device according to claim 6, wherein the controller has a configuration to define the measurement-result-correction target region by comparing measurement results of a fifth measurement gate signal of the measurement gate signals, a sixth measurement gate signal at a measurement position having a symmetric relation with a measurement position of the fifth measurement gate signal about the dividing line, a seventh measurement gate signal at a position having a symmetric relation with the measurement position of the fifth measurement gate signal about a symmetric axis passing through the center of the reaction region and perpendicular to the dividing line, and an eighth measurement gate signal at a position having a symmetric relation with the measurement position of the sixth measurement gate signal about the symmetric axis.

9. The analysis device according to claim 8, wherein the controller has a configuration to determine the measurement-result-correction target region by comparing measurement results of measurement gate signals of tracks adjacent to each other.

10. The analysis device according to claim 8, wherein, when it is determined that the measurement position of the fifth measurement gate signal is defined as the measurement-result-correction target region, the controller has a configuration to calculate an average of the number of the fine particles obtained from each of the sixth measurement gate signal, the seventh measurement gate signal, and the eighth measurement gate signal, and corrects the number of the fine particles obtained from the fifth measurement gate signal to the average.

11. An analysis method using the analysis device of claim 1:

the analysis method steps comprising:
rotating the specimen analysis disc with the turntable drive unit;
emitting the laser light to the first, the second, the third, and the fourth measurement gate signals per track;
receiving the reflected light from the reaction region with the receiver and generating a reception level signal of the reflected light with the generator;
counting the number of the fine particles per measurement gate signal from the reception level signal;
comparing the first, the second, the third, and the fourth measurement results in the reaction region, and
defining whether the first, the second, the third, and the fourth measurement result is a measurement-result-correction target region for correcting the number of the fine particles.

* * * * *